United States Patent
Stein et al.

(10) Patent No.: US 8,975,233 B2
(45) Date of Patent: *Mar. 10, 2015

(54) METHODS FOR RENAL DENERVATION

(75) Inventors: Emily A. Stein, San Leandro, CA (US); Kondapavulur T. Venkateswara-Rao, San Jose, CA (US); Michael A. Evans, Palo Alto, CA (US)

(73) Assignee: Northwind Medical, Inc., San Jose, CA (US)

( * ) Notice: Subject to any disclaimer, the term of this patent is extended or adjusted under 35 U.S.C. 154(b) by 338 days.

This patent is subject to a terminal disclaimer.

(21) Appl. No.: 13/014,700

(22) Filed: Jan. 26, 2011

(65) Prior Publication Data

US 2011/0182912 A1 Jul. 28, 2011

Related U.S. Application Data

(60) Provisional application No. 61/336,838, filed on Jan. 26, 2010.

(51) Int. Cl.

| A61K 31/704 | (2006.01) |
| A61M 25/00 | (2006.01) |
| A61K 31/7048 | (2006.01) |
| A61B 5/0215 | (2006.01) |
| A61B 5/00 | (2006.01) |
| A61B 17/22 | (2006.01) |
| A61B 19/00 | (2006.01) |
| A61M 25/04 | (2006.01) |
| A61M 25/10 | (2013.01) |

(52) U.S. Cl.
CPC ........ *A61M 25/0084* (2013.01); *A61K 31/7048* (2013.01); *A61B 5/0215* (2013.01); *A61B 5/4839* (2013.01); *A61B 2017/22054* (2013.01); *A61B 2017/22061* (2013.01); *A61B 2017/22067* (2013.01); *A61B 2019/5276* (2013.01); *A61B 2019/528* (2013.01); *A61M 25/04* (2013.01); *A61M 2025/0086* (2013.01); *A61M 2025/0087* (2013.01); *A61M 2025/1047* (2013.01)
USPC .......................... 514/25; 514/17.7; 424/137.1

(58) Field of Classification Search
None
See application file for complete search history.

(56) References Cited

U.S. PATENT DOCUMENTS

| 4,578,061 A | 3/1986 | Lemelson |
| 5,354,279 A | 10/1994 | Höfling |
| 5,681,281 A | 10/1997 | Vigil et al. |
| 5,693,029 A | 12/1997 | Leonhardt |
| 5,746,716 A | 5/1998 | Vigil et al. |
| 6,217,554 B1 | 4/2001 | Green |
| 6,302,870 B1 | 10/2001 | Jacobsen et al. |
| 6,692,466 B1 | 2/2004 | Chow et al. |
| 6,849,597 B2 | 2/2005 | Murata et al. |
| 6,860,867 B2 | 3/2005 | Seward et al. |
| 6,978,174 B2 | 12/2005 | Gelfand et al. |
| 7,070,606 B2 | 7/2006 | Seward |
| 7,127,284 B2 | 10/2006 | Seward |
| 7,155,284 B1 | 12/2006 | Whitehurst |
| 7,162,303 B2 | 1/2007 | Levin et al. |
| 7,363,076 B2 | 4/2008 | Yun et al. |
| 7,465,298 B2 | 12/2008 | Seward et al. |
| 7,547,294 B2 | 6/2009 | Seward et al. |
| 7,559,923 B2 | 7/2009 | Seward et al. |
| 7,615,049 B2 | 11/2009 | West et al. |
| 7,647,115 B2 | 1/2010 | Levin et al. |
| 7,653,438 B2 | 1/2010 | Deem et al. |
| 7,666,163 B2 | 2/2010 | Seward et al. |
| 7,670,329 B2 | 3/2010 | Flaherty et al. |
| 7,691,080 B2 | 4/2010 | Seward et al. |
| 7,717,948 B2 | 5/2010 | Demarais et al. |
| 7,744,584 B2 | 6/2010 | Seward et al. |
| 7,756,583 B2 | 7/2010 | Demarais et al. |
| 7,853,333 B2 | 12/2010 | Demarais |
| 7,873,417 B2 | 1/2011 | Demarais et al. |
| 7,879,011 B2 | 2/2011 | Chang |
| 8,131,371 B2 | 3/2012 | Demarais et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2002/0072706 A1 | 6/2002 | Hiblar et al. |
| 2002/0115992 A1 | 8/2002 | Utley et al. |

(Continued)

FOREIGN PATENT DOCUMENTS

| WO | WO 8403623 A1 | 9/1984 |
| WO | WO 2004030718 A2 | 4/2004 |

(Continued)

OTHER PUBLICATIONS

PCT Application No. PCT/US2011/022653 (EVANS001PCT), International Search Report and Written Opinion, Apr. 11, 2011.

Converse et al. Sympathetic overactivity in patients with chronic renal failure. N. Engl. J. Med., Dec. 31, 1992, vol. 327, No. 27, pp. 1912-1918.

(Continued)

*Primary Examiner* — Robert C Hayes

(57) ABSTRACT

Various agents are described to denerve, modulate, or otherwise affect the renal nerves and other neural tissue. Also, various delivery devices are described to deliver an agent locally to the renal nerves. The delivery devices are positioned in the renal artery and penetrate into the wall of the renal artery to deliver the agent to the renal nerves. The delivery devices may be used to deliver the agent according to longitudinal position, radial position, and depth of the renal nerves relative to the renal artery. In addition, various methods are described to denervate, modulate, or otherwise affect the renal nerves and other neural tissue.

10 Claims, 20 Drawing Sheets

(56) References Cited

U.S. PATENT DOCUMENTS

| | | |
|---|---|---|
| 2003/0171734 A1 | 9/2003 | Seward et al. |
| 2004/0059179 A1 | 3/2004 | Maguire et al. |
| 2004/0064093 A1 | 4/2004 | Hektner et al. |
| 2004/0156931 A1 | 8/2004 | Burch et al. |
| 2004/0162542 A1 | 8/2004 | Wilber et al. |
| 2005/0182071 A1 | 8/2005 | Seward et al. |
| 2005/0245862 A1 | 11/2005 | Seward et al. |
| 2006/0189941 A1 | 8/2006 | Seward et al. |
| 2006/0217680 A1 | 9/2006 | Barath |
| 2006/0259005 A1 | 11/2006 | Konstantino et al. |
| 2007/0083239 A1 | 4/2007 | Demarais et al. |
| 2007/0112327 A1 | 5/2007 | Yun et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0213761 A1 | 9/2007 | Murphy et al. |
| 2007/0250035 A1 | 10/2007 | El-Nounou et al. |
| 2008/0004596 A1 | 1/2008 | Yun et al. |
| 2008/0213331 A1 | 9/2008 | Gelfand et al. |
| 2009/0054527 A1 | 2/2009 | Burch et al. |
| 2009/0062359 A1 | 3/2009 | Burch et al. |
| 2009/0076409 A1 | 3/2009 | Wu et al. |
| 2009/0111792 A1 | 4/2009 | Burch et al. |
| 2009/0270906 A1 | 10/2009 | Hossainy |
| 2010/0010567 A1 | 1/2010 | Deem et al. |
| 2010/0222854 A1 | 9/2010 | Demarais |
| 2010/0249773 A1 | 9/2010 | Clark et al. |
| 2010/0249859 A1 | 9/2010 | DiLorenzo |
| 2011/0104060 A1 | 5/2011 | Seward |
| 2011/0104061 A1 | 5/2011 | Seward |
| 2011/0112400 A1 | 5/2011 | Emery et al. |
| 2011/0200171 A1 | 8/2011 | Beetel et al. |
| 2011/0207758 A1 | 8/2011 | Sobotka et al. |
| 2011/0208173 A1 | 8/2011 | Sobotka et al. |
| 2011/0208175 A1 | 8/2011 | Sobotka et al. |
| 2011/0264011 A1 | 10/2011 | Wu et al. |
| 2011/0264075 A1 | 10/2011 | Leung et al. |
| 2012/0130289 A1 | 5/2012 | Demarais et al. |
| 2012/0130345 A1 | 5/2012 | Levin et al. |
| 2012/0197198 A1 | 8/2012 | Demarais et al. |

FOREIGN PATENT DOCUMENTS

| | | |
|---|---|---|
| WO | WO 2007127488 A1 | 11/2007 |
| WO | WO2009103932 A1 * | 8/2009 |
| WO | WO 2010078175 A1 | 7/2010 |

OTHER PUBLICATIONS

Xiao et al. Ionic mechanism of ouabain-induced concurrent apoptosis and necrosis in individual cultured cortical neurons. J. Neurosci., Feb. 15, 2002, vol. 22, No. 4, pp. 1350-1362.

Schlaich et al. Renal sympathetic-nerve ablation for uncontrolled hypertension. N. Engl. J. Med., Aug. 27, 2009, vol. 361, No. 9, pp. 932-934.

Schlaich et al. Renal denervation as a therapeutic approach for hypertension. Hypertension, Dec. 2009, vol. 54, pp. 1195-1201.

Esler. Pathophysiology of the human sympathetic nervous system in cardiovascular diseases: the transition from mechanisms to medical management. J. Appl. Physiol., Feb. 2010, vol. 108, pp. 227-237.

Esler et al. Point: Chronic activation of the sympathetic nervous system is the dominant contributor to systemic hypertension. J. Appl. Physiol., Dec. 2010, vol. 109, pp. 1996-1998.

Prescribing Information, DigiFab Digoxin Immune Fab (Ovine), BTG International Inc., Jan. 2012. http://www.digifab.us/viewpdf.do?documentld=3.

Product Monograph, DIGIBIND Digoxin Immune Fab (Ovine), GlaxoSmithKline Inc., May 2009. http://www.gsk.ca/english/docs-pdf/Digibind_PM_20090525_EN.pdf.

Antibody Resource, Digoxin Antibodies (including mouse, rabbit, sheep, and goat), http://www.antibodyresource.com/search/Antibodies/2d250441-cff9-5c2a-8fd9-73a808ceac7b/digoxin (retrieved Apr. 28, 2014).

Sigma-Aldrich, Inc., Product Information, Monoclonal Anti-Digoxin (mouse), http://www.sigmaaldrich.com/content/dam/sigma-aldrich/docs/Sigma/Datasheet/3/d8156dat.pdf (retrieved Apr. 28, 2014).

MyBioSource, Inc., Datasheet, Digoxin antibody (mouse), http://www.mybiosource.com/datasheet.php?products_id=190115&pfd=true (retrieved Apr. 28, 2014).

PCT Application No. PCT/US2012/062006 (NORTH004PCT), International Search Report and Written Opinion, Feb. 14, 2013.

PCT Application No. PCT/US2013/039904 (NORTH005PCT), International Search Report and Written Opinion, Aug. 13, 2013.

DiBona GF. Nervous kidney. Interaction between renal sympathetic nerves and the renin-angiotensin system in the control of renal function. Hypertension, Dec. 2000;36(6):1083-8, PMID: 11116129.

Tegner R et al. Morphological study of peripheral nerve changes induced by chloroquine treatment. Acta Neuropathol, 1988;75(3):253-60, PMID:2831692.

PCT application PCT/US2014/030804, Oct. 16, 2014, ISR/WO.

Riaz et al., Digoxin Use in Congestive Heart Failure, Drugs, vol. 55, No. 6, pp. 747-758, Jun. 1998.

* cited by examiner

METHODS FOR RENAL DENERVATION

CROSS-REFERENCE TO RELATED APPLICATIONS

This application claims the benefit of U.S. provisional application Ser. No. 61/336,838, filed Jan. 26, 2010, which is incorporated by reference.

BACKGROUND

A blood vessel or other bodily passage may be used to access parts of the body to deliver an agent to a target site in the wall of the vessels. For example, the renal arteries may be used as access pathways to deliver a therapeutic agent to the renal nerves, which run within the wall of the renal arteries. However, it may be difficult to deliver therapeutic agents with sufficient precision to the renal nerves. One approach is to "flood" the entire region about the circumference of the renal artery using the agent. This approach uses more of the agent than is necessary and may be toxic to the patient or surrounding tissues. Moreover, the toxicity concerns can also significantly limit the selection of particular therapeutic agents to kill nerves and the ability to provide effective treatment.

What is needed is a way of locally delivering the amount of an agent needed to effect a desired therapeutic response while reducing injury or harm to surrounding tissue. What is also needed is a way of delivering an agent to a target site within the wall of a blood vessel with increased precision and a way of removing or neutralizing excess amount of agents to reduce potential toxicity effects or vascular trauma.

Nerve denervation may be used to manage hypertension, congestive heart failure, endstage renal disease, and other conditions. Radio frequency (RF) ablation of the renal nerves has been practiced and often lacks fine control, and may cause unintended damage to neighboring tissue such as the endothelium lining blood vessels and smooth muscles that constitute blood vessel walls, resulting in vessel injury or occlusion.

What is needed are methods, devices, and agents for renal denervation which offer greater control over the denervation process than RF ablation or bolus injection, and the appropriate chemistry for controlled delivery and subsequent neutralization to reduce vessel occlusion, spasm, or other tissue damage.

SUMMARY

A method for killing targeted nerve cells in a mammal is described. The method includes delivering a potentiating agent locally to the nerve cells in an amount sufficient to potentiate the toxicity effects of an excitatory signal induced by a stimulant. The method also includes delivering a stimulant locally to the nerve cells in an amount sufficient to overstimulate the nerve cells to promote apoptosis of the nerve cells.

DETAILED DESCRIPTION

Figure 1A:
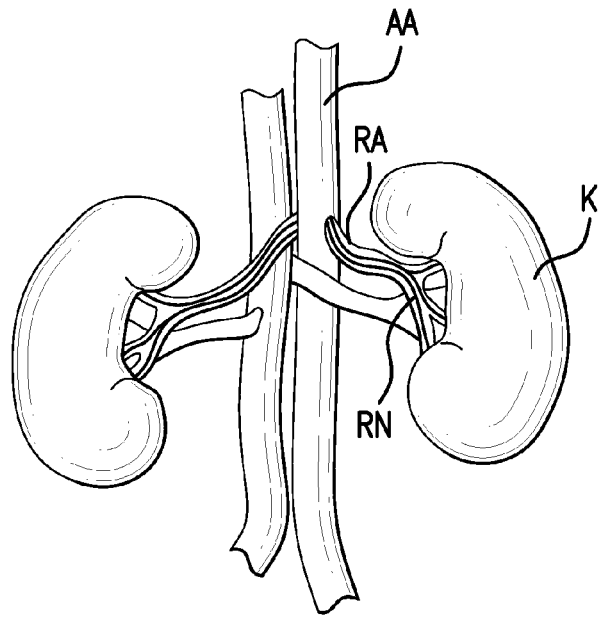
FIG. 1A shows a front view of an abdominal aorta, a renal artery, renal nerves, and a kidney.

Methods, apparatuses, agents, and methods of delivery to provide temporary and permanent nerve blockage are described, to denerve the nervous system at specific sites and kill nerve cells to treat disease. Delivery systems and agents are described that provide site-specific treatment and control so that the controlling effects are localized and can be adjusted over time to interrupt or modulate the neural response and up or down regulate organ function. These agents are also formulated in such a way that they target or have an affinity for neural matter. Agents may also be delivered in a time-dependent release configuration that focuses treatment in a sustained manner on the desired neural matter while reducing negative effects on the surrounding tissue and related function, and protecting the blood vessel linings and surrounding tissues. Agents may also be delivered in combination or in sequence to provide enhanced agent bioavailability or bioactivity on targeted neural matter. Some neural modulation agents will have greater effect when delivered by methods that use mechanical, thermal, electric, magnetic, electromagnetic, cryogenic, or other energy forms to provide greater energy input, bioavailability, permeation, thermal, or chemical activity.

Various agents, chemicals, proteins and toxins have been used to provide temporary nerve blockage. Some of these agents include site 1 sodium channel blockers such as tetrodotoxin (TTX), saxitoxin (STX), decarbamoyl saxitoxin, vanilloids, and neosaxitoxin are used as local anesthetic formulations. Other agents such as lidocaine may be used as temporary nerve blockage agents, whereas conotoxins may also provide temporary nerve blockade. Other agents not known to provide nerve blockade are inotropic drugs such as cardiac glycosides, which have been used to treat congestive heart failure and arrhythmias, and more recently the hoiamides have been identified to display inotropic properties. These agents are useful to achieve temporary nerve blockage, and in excess or in combination with inotropic agents, achieve long-term nerve blockade and potentiate nerve cell damage. Devices, agents and/or control methods are required to achieve permanent nerve blockage, denervation and/or neuromodulation to control bodily functions such as heart rate, hypertension, metabolic function, pain, arthritis, and the like. In addition, compounds or agents are needed that can permanently impair the function of nerve cells or specifically kill nerve cells and induce apoptosis, thus affecting the neural conduction pathways. Examples of agents are neurotoxins such as tetrodotoxin, serotoxin, ω-conotoxin; nerve agents such as organophosphates, sarin, and others; antagonist antibodies against nerve growth hormones such as nerve growth factor (NGF), the prototypical member of the neurotropin family; excitatory amino acids such as glutamate and domoic acid in excess or in combination with inotropic drugs. Excess concentrations of or combinations of more than one channel blocker such as lithium, carbamazepine, and verapamil can be used to promote nerve cell death.

Devices to deliver site-specific denervation agents require precise control of target location, tissue depth and location of neural matter. Such methods and devices may include catheters integrated with hollow injection ports or solid protrusions coated with agents and positioning structures such as inflatable balloons or self-expanding, spring-like structures employing standard catheter-based delivery and deployment methods used in minimally-invasive interventional procedures. In one method, mechanically expanding, self expanding devices, or braided structures formed from materials such as spring steel, nickel titanium or the like, can be placed at the desired site and activated or released in position to allow delivery of agents in predetermined patterns at discrete, non-contiguous sites along the arterial walls at specific depths from the luminal surface where neural matter is resident or where neural signal pathways are located. Such expanding device may allow for perfusion during treatment and may also be utilized to provide a stop or indexing mechanism to provide the user with a predetermined length of treatment from the aortic ostium.

The devices may also be balloons with solid protrusions to perfuse or inject agents into tissue or the wall of a vessel, or tube and syringe delivery methods. A braided structure may be used to anchor and assist in fixing a delivery catheter in a blood vessel such as the renal artery and deliver agents to one or more sites along the artery substantially simultaneously. The depth, linear spacing, and circumferential spacing of the sites for delivery is important to achieve the desired therapeutic effect while preserving vessel structure (endothelial cells, intima, and media) and function while reducing injury to the delicate vessel lining caused by the application of thermal, RF, or other forms of energy. Additionally, the braided structure may be constructed from materials that conform to the vessels at low expansion pressures to position the protrusions for agent delivery while reducing endothelial denudation. The braided structure may also include features for non-obstructive function (blood flow perfusion in the case of renal arteries, or bile secretion in the liver) during denervation.

Other delivery systems may include balloons and implantable systems made from biodegradable or coated non-biodegradable devices such as stents with protruding structures (solid protrusions or tubes) to deliver nerve denervating drugs or molecules that affect neural blockade and/or control nerve signaling while simultaneously treating atherosclerotic disease and the like. Ultrasound or other forms of mechanical agitation can be added to delivery systems to further aid and enhance agent delivery, diffusion and activity into the adventitia.

Other delivery methods may include localized treatment packaging the agents in a delivery medium that can regulate the delivery rate of agents or has an impact on the agent's half-life, while reducing impact to surrounding tissue. Such configurations may include time-release microspheres from biodegradable polymers or hydrogels and fluids that have a specific decay rates and delivery profiles. The potential for nerve fiber regeneration may also be addressed by time-release systems that can continue to kill or block nerve fibers that regenerate over time.

In order to more precisely locate target neural matter, various diagnostic devices may be used in combination with delivery systems to deliver therapy. Such imaging modalities include computed tomography (CT), magnetic-resonance imaging (MRI), fluoroscopy, or ultrasound. Ultrasound may be external or internally guided, and may use various agents such as ultrasound contrast or ultrasound microbubble agents to aid in imaging neural matter, their location and sites for denervation. Ultrasound can measure both vessel wall thickness and placement of delivery devices to ensure accurate delivery. Unlike angiography, ultrasound can also image plaque and help determine the depth of penetration needed to reach the neural matter. For example, in healthy arteries, the neurons that are present mostly in the adventitial regions of the vessel wall are located about 2-3 millimeters from the inner lumen of the blood vessel. When diseased, this distance increases by the thickness of plaque. Atherosclerotic plaque is often unevenly distributed along the circumference and length of the vessel. Ultrasound guided imaging may help locate the target location for denervation.

Electroanatomical mapping and MRI methods may also be used to identify the target location and deliver agents. In electroanatomical mapping, a mapping transducer in conjunction with an external electromagnetic field is used to map the electrical conduction pathways and neuron signal activity surrounding blood vessels and tissue. External (coil magnets) and internal (catheter-based coils) MRI imaging methods may also be used to map the neural matter and neural signal activity.

Another aspect of delivery of these agents is to reduce detrimental effects to surrounding tissue and organs. The delivery systems and methods described may include a neutralizer flush system to inactivate any agent that gets beyond the desired delivery site or any agent that does not bind target neurons within the target site. To provide this control and neutralizer function, the delivery systems may include dual isolation balloons where agent is delivered between balloons or systems that aspirate or neutralize any excess material or fluids during or after agent delivery. Polymer delivery systems may also incorporate materials to deactivate or destroy residual agents in a predetermined manner or time using coatings such as oxidizers or the like for programmed deactivation or destruction. Alternatively, delivery agents may be formulated in a time-release material that when deployed, the unbound agent is flushed by the kidneys.

Figure 1B:
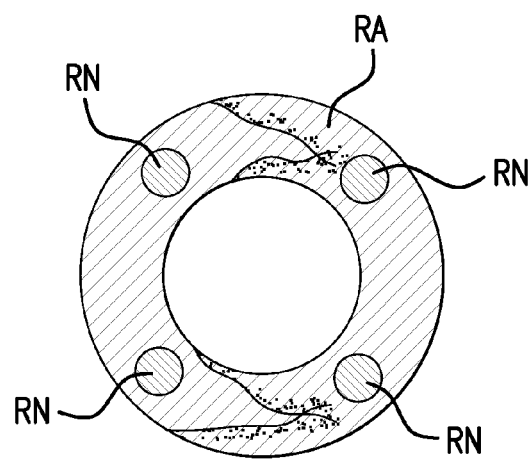
FIG. 1B shows a cross-sectional view of a renal artery RA and renal nerves RN.

FIG. 1A shows a front view of an abdominal aorta AA, a renal artery RA, renal nerves RN, and a kidney K. The renal nerves run lengthwise within the wall of the renal artery. FIG. 1B shows a cross-sectional view of a renal artery RA and renal nerves RN.

Various delivery devices are described for targeted delivery of an agent locally to the renal nerves. The delivery devices are positioned in the renal artery and penetrate into the walls of the renal artery to deliver the agent to the renal nerves. The delivery devices may be used to deliver the agent according to three parameters:

(1) Longitudinal position. The renal nerves run lengthwise along the renal artery. Instead of delivering an agent to the nerves at just one longitudinal position, the delivery devices described may be used to deliver an agent to the nerves at multiple discrete (non-contiguous) longitudinal positions along a length of the renal artery.

(2) Radial position. The renal nerves are located at varying radial positions relative to a circumference of the renal artery. Instead of delivering agents to just one radial position, the delivery devices described may be used to simultaneously deliver agents to multiple radial positions in the renal artery.

(3) Depth. The renal nerves are located at varying depths relative to an inner wall of the renal artery. Instead of delivering agents to a fixed depth or distance, the delivery devices described may be used to deliver agents to a range of desired depths or distances. The desired depths may vary along the longitudinal axis of the delivery device to account for the anatomical changes along the length of the renal artery.

The delivery devices described are capable of delivering the agent at multiple points that are discrete and non-contiguous along the length of the renal nerves, effectively increasing the amount of the renal nerves that are treated or exposed to the agent. The delivery devices described also allow for delivering small amounts of the agent to be used, by delivering the agent in a more targeted and precise manner.

Figure 2A:
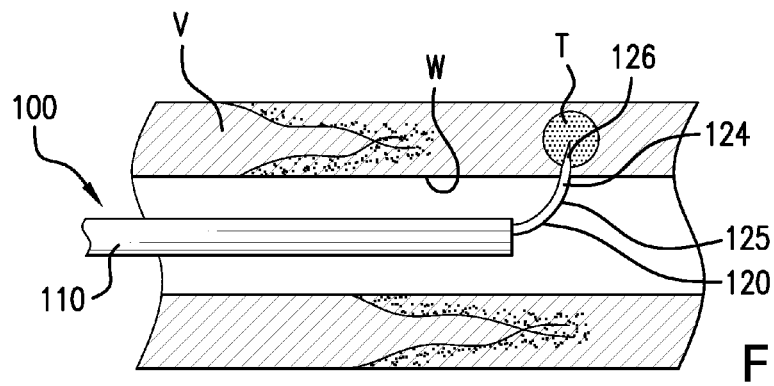
FIGS. 2A-2H show various embodiments of a delivery device.

FIG. 2A shows one embodiment of a delivery device 100. Delivery device 100 includes a catheter 110 and a delivery tube 120 slidably coupled within catheter 110. Delivery tube 120 includes a distal end 124 with a delivery point 126. Delivery tube 120 may include a delivery lumen 125. Alternatively, delivery tube 120 may be solid instead of hollow.

Delivery tube 120 is outwardly biased from a longitudinal axis of catheter 110. Delivery tube 120 may be made of a shape-memory and super-elastic alloy such as nickel titanium, stainless steel, or other suitable materials of sufficient strength and toughness to achieve a desired depth of penetration. Delivery tube 120 may be preshaped to a desired three-dimensional configuration, using shape-memory or super-elastic properties of nickel-titanium or spring properties of steels or other alloys used to make springs, so that once the catheter is retracted, delivery tube 120 makes contact with and penetrates into wall W. Delivery point 126 may be sharp. Delivery lumen 125 may have an inner surface that is coated or treated with polyethylene or other suitable material to reduce the loss or degradation of agents from adhesion inside delivery lumen 125 while delivering the agent Delivery tube 120 is delivered retracted inside catheter 110, with delivery point 126 unexposed. Delivery tube 120 is positioned in a vessel V at the longitudinal position of a target site T. Catheter 110 may also be rotated to position delivery point 126 at a radial position of target site T. Delivery tube 120 is then extended from catheter 110 to expose delivery point 126 and penetrate into wall W. Delivery tube 120 is extended until delivery point 126 is positioned at a depth of target site T. Delivery tube 120 then delivers an agent through delivery lumen 125 to target site T. Alternatively, delivery point 126 may be treated or coated with an agent which is capable of being absorbed by target site T.

Figure 2B:
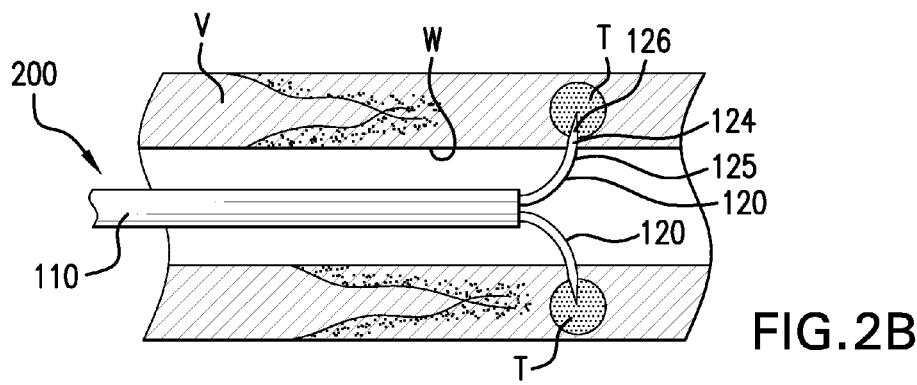

FIG. 2B shows another embodiment of a delivery device 200. Delivery device 200 is similar to delivery device 100, but includes a plurality of delivery tubes 120. Delivery tubes 120 may each be independently extended and retracted from catheter 110. Delivery device 200 allows multiple target sites T at the same longitudinal position to be treated at the same time.

Figure 2C:
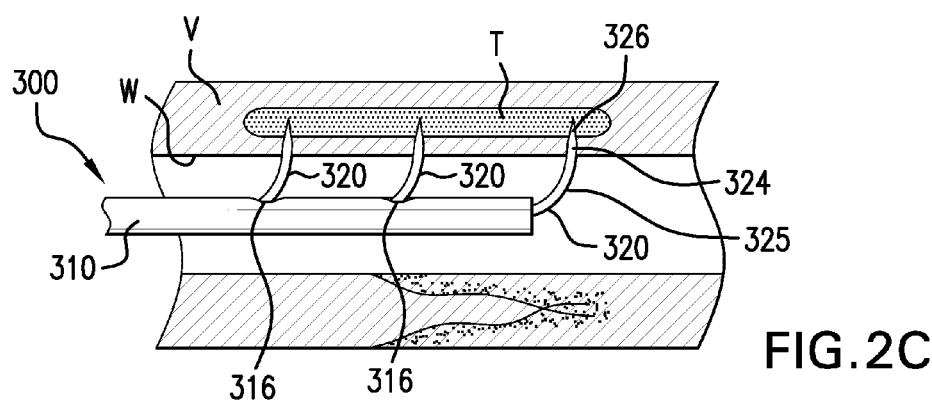
Figure 2D:
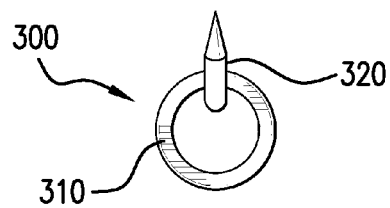

FIGS. 2C-2D show another embodiment of a delivery device 300. FIG. 2C shows a side view of delivery device 300. FIG. 2D shows an end view of delivery device 300. Delivery device 300 includes a catheter 310 with a plurality of ports 316. Ports 316 are formed at the same angle relative to a longitudinal axis of catheter 310. Delivery device 300 also includes a plurality of delivery tubes 320 slidably coupled within catheter 310. Delivery tubes 320 may be evenly or irregularly spaced. Delivery tubes 320 each include a distal end 324 with a delivery point 326. Delivery tubes 320 may each include a delivery lumen 325. Alternatively, one or more delivery tubes 320 may be solid instead of hollow.

Delivery tubes 320 are outwardly biased from a longitudinal axis of catheter 310. Delivery tubes 320 may be made of a shape-memory alloy such as nickel titanium, or other suitable material. Delivery tubes 320 may be preshaped to a desired three-dimensional configuration, using shape-memory or super-elastic properties of nickel-titanium or spring properties of steels or other alloys used to make springs, so that once the catheter is retracted, delivery tubes 320 make contact with and penetrate into wall W. Delivery points 326 may be sharp. Delivery lumens 325 may have inner surfaces that are coated or treated with polyethylene or other suitable material to reduce the loss or degradation of agents from adhesion inside delivery lumens 325.

Delivery tubes 320 are delivered retracted inside catheter 310, with delivery points 326 unexposed. Delivery tubes 320 are positioned in a vessel V at the longitudinal position of a target site T. Catheter 310 may also be rotated to position delivery points 326 at a radial position of target site T. Delivery tubes 320 are then extended from catheter 310 through ports 316 to expose delivery points 326 and penetrate into wall W. Delivery tubes 320 may be extended until delivery points 326 are positioned at a depth of target site T. Delivery tubes 320 then deliver an agent through delivery lumens 325 to target site T. Alternatively, delivery points 326 may be treated or coated with an agent which is capable of being absorbed by target site T. Delivery device 300 allows a longer target site T at a similar radial position to be treated at the same time.

Figure 2E:
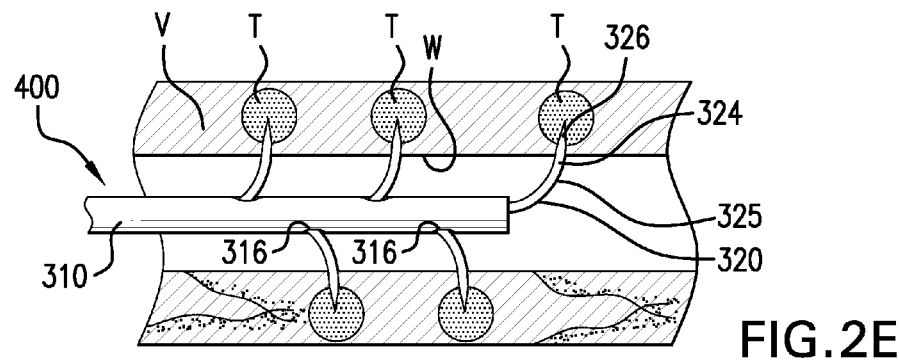
Figure 2F:
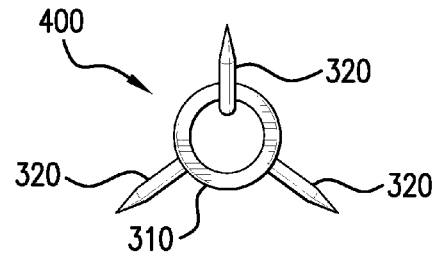

FIGS. 2E-2F show another embodiment of a delivery device 400. FIG. 2E shows a side view of delivery device 400. FIG. 2F shows an end view of delivery device 400. Delivery device 400 is similar to delivery device 300, but includes a plurality of ports 316 that are formed at different angles relative to a longitudinal axis of catheter 310. Delivery tubes 320 thus extend at different angles from catheter 310. Delivery device 400 allows longer target sites T at multiple radial positions to be treated at the same time.

Figure 2G:
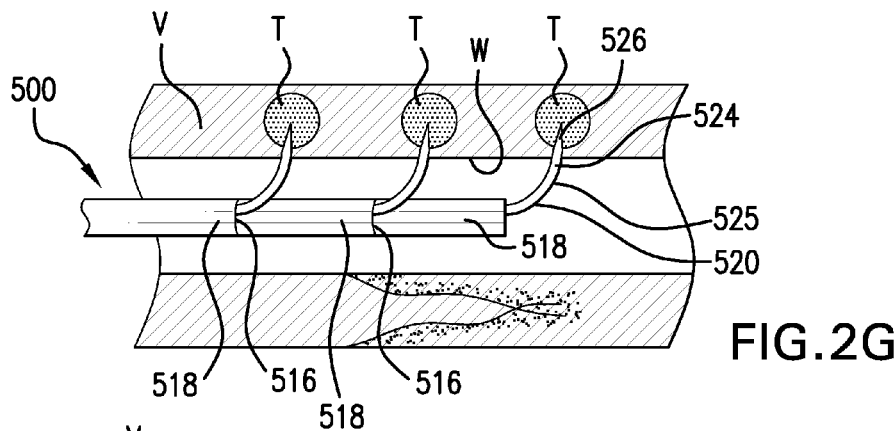

FIG. 2G shows another embodiment of a delivery device 500. Delivery device 500 includes a catheter 510 with a plurality of ports 516, with each port 516 formed on a separate catheter section 518. Each catheter section 518 may be slidably disposed within the catheter section 518 before it. Delivery device 500 also includes a plurality of delivery tubes 520 slidably coupled within catheter 510. Delivery tubes 520 each include a distal end 524 with a delivery point 526. Delivery tubes 520 may each include a delivery lumen 525. Alternatively, one or more delivery tube 520 may be solid instead of hollow.

Delivery tubes 520 are outwardly biased from a longitudinal axis of catheter 510. Delivery tubes 520 may be made of a shape-memory alloy such as nickel titanium, or other suitable material. Delivery tubes 520 may be preshaped to a desired three-dimensional configuration, using shape-memory or super-elastic properties of nickel-titanium or spring properties of steels or other alloys used to make springs, so that once the catheter is retracted, delivery tubes 520 make contact with and penetrate into wall W. Delivery points 526 may be sharp. Delivery lumens 525 may have inner surfaces that are coated or treated with polyethylene or other suitable material to reduce the loss or degradation of agents from adhesion inside delivery lumens 525.

Delivery tubes 520 are delivered retracted inside catheter 510, with delivery points 526 unexposed. Each catheter section 518 may be independently extended and refracted to position delivery tubes 520 at the longitudinal positions of target sites T. Each catheter section 518 may also be independently rotated to position delivery points 526 at the radial positions of target sites T. Delivery tubes 520 are then extended from catheter sections 518 through ports 516 to expose delivery points 526 and penetrate into wall W. Delivery tubes 520 may each be independently extended until delivery points 526 are positioned at the depths of target sites T. Delivery tubes 520 then deliver an agent through delivery lumens 525 to target sites T. Alternatively, delivery points 526 may be treated or coated with an agent which is capable of being absorbed by target sites T. Delivery device 500 allows multiple target sites with different longitudinal positions, radial positions, and depths to be treated at the same time.

Figure 2H:
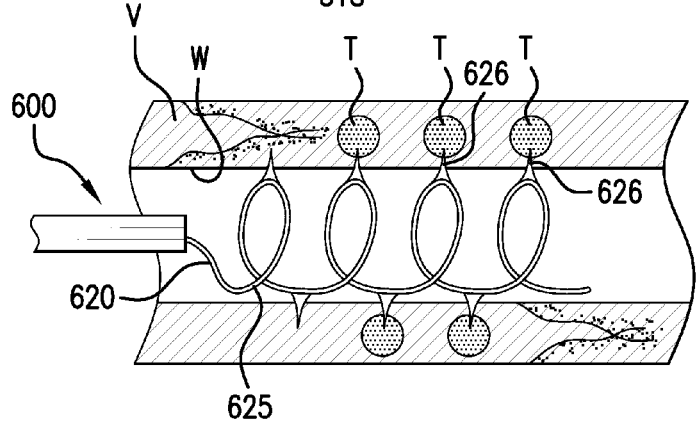

FIG. 2H shows another embodiment of a delivery device 600. Delivery device 600 includes a catheter 610 with a coil 620 having along its length one or more delivery points 626. Coil 620 also includes a delivery lumen 625.

Coil 620 is self-expanding. Coil 620 may be made of a shape-memory alloy such as nickel titanium, or any other suitable material. Coil 620 may be preshaped to a desired three-dimensional configuration, using shape-memory or super-elastic properties of nickel-titanium or spring properties of steels or other alloys used to make springs, so that once the catheter is retracted, coil 620 expands and makes contact with and delivery points 626 penetrate into wall W. Delivery points 626 may be sharp. Delivery lumen 625 may have an inner surface that is coated or treated with polyethylene or other suitable material to reduce the loss or degradation of agents from adhesion inside delivery lumen 625.

Coil 620 is delivered in an unexpanded configuration inside catheter 610, with delivery points 626 unexposed. Coil 620 is positioned in a vessel V at the longitudinal position of target sites T. Catheter 610 is then pulled back to allow coil 620 to open and expose delivery points 626 to penetrate into wall W. Coil 620 then delivers an agent through delivery lumen 625 to target sites T. Alternatively, delivery points 626 may be treated or coated with an agent which is capable of being absorbed by target sites T.

Figure 3A:
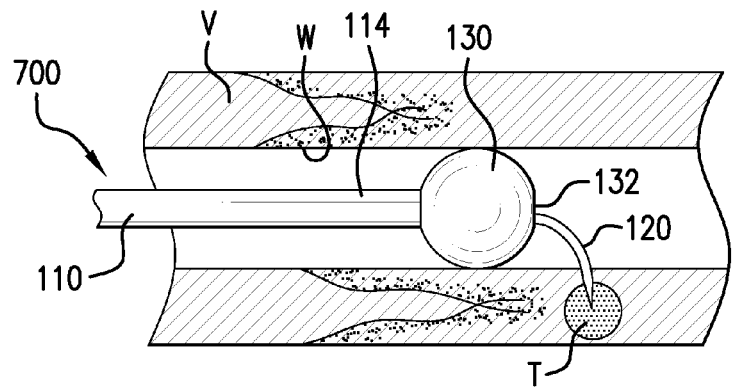
FIGS. 3A-3G show various embodiments of a delivery device.

FIG. 3A shows another embodiment of a delivery device 700. Delivery device 700 is similar to delivery device 100, but also includes a balloon 130 coupled to a distal end 114 of catheter 110.

Balloon 130 may have a port 132 through which delivery tube 120 can pass. Balloon 130 may be inflated and deflated through an inflation lumen 135. When inflated, balloon 130 may anchor distal end 114 of catheter 110 within vessel V.

Figure 3B:
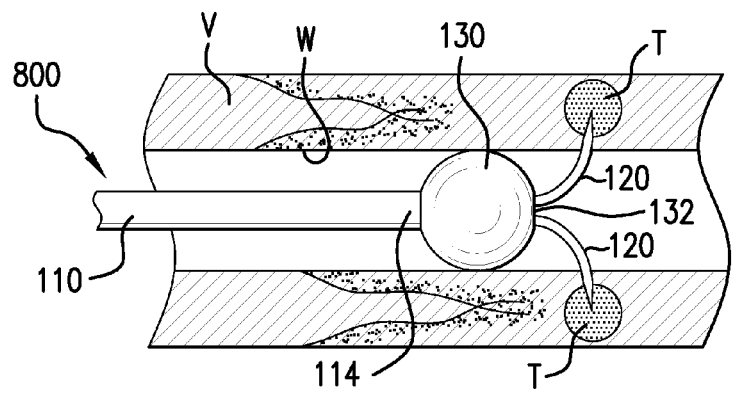

FIG. 3B shows another embodiment of a delivery device 800. Delivery device 800 is similar to delivery device 200, but also includes a balloon 130 coupled to a distal end 114 of catheter 110.

Figure 3C:
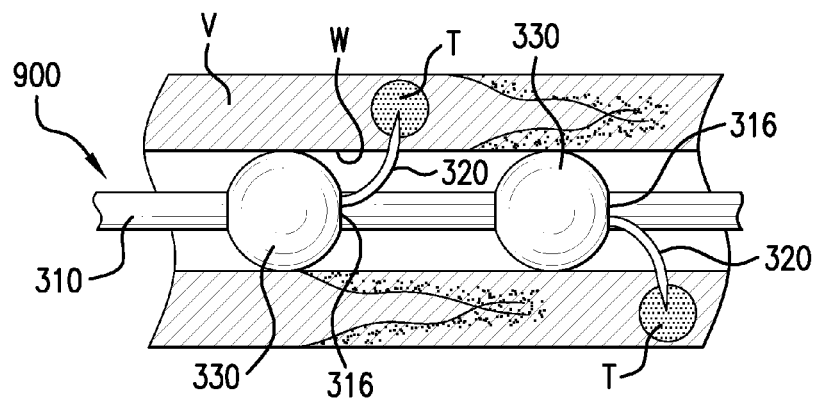

FIG. 3C shows another embodiment of a delivery device 900. Delivery device 900 is similar to delivery device 400, but includes a balloon 330 adjacent to each port 316.

Figure 3D:
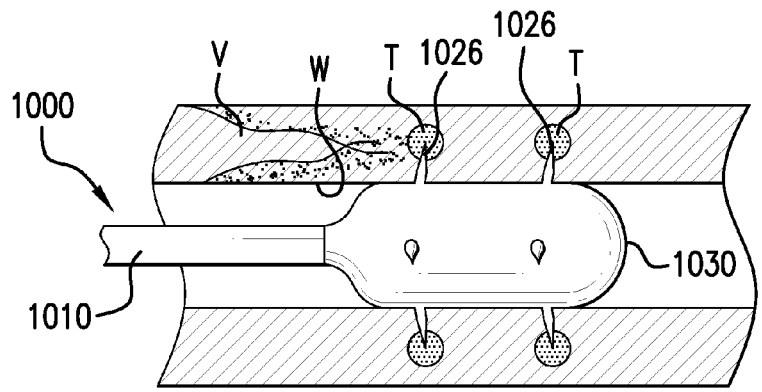

FIG. 3D shows another embodiment of a delivery device 1000. Delivery device 1000 includes a catheter 1010 with a balloon 1030. A plurality of delivery points 1026 is coupled to the surface of balloon 1030. Catheter 1010 includes a delivery lumen 1025 in fluid communication with the delivery points 1026. Catheter 1010 also includes an inflation lumen 1035 coupled to the balloon.

Delivery points 1026 may be sharp. Delivery lumen 1025 may be coated or treated with polyethylene or other suitable material to reduce the loss of agents from adhesion inside delivery lumen 1025.

Balloon 1030 is delivered in a deflated configuration inside catheter 1010, with delivery points 1026 unexposed. Balloon 1030 is positioned in a vessel V at the longitudinal position of target sites T. Catheter 1010 is then pulled back and balloon 1030 inflated to expose delivery points 1026 to penetrate into wall W. Delivery points 1026 then deliver an agent to target sites T.

Figure 3E:
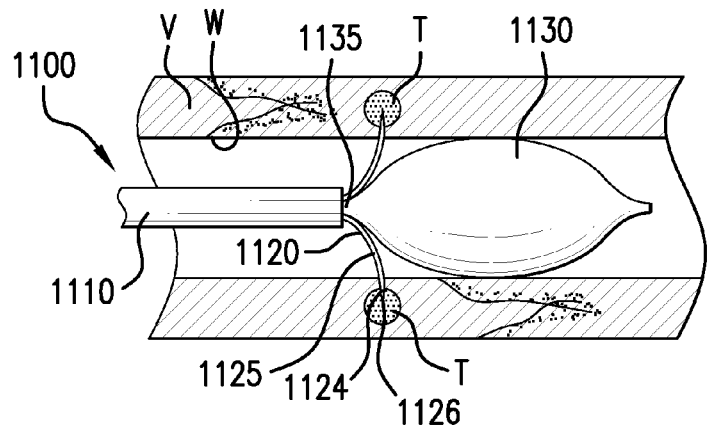

FIG. 3E shows one embodiment of a delivery device 1100. Delivery device 1100 includes a catheter 1110 and a plurality of delivery tubes 1120 slidably coupled within catheter 1110. Delivery tubes 1120 each include a distal end 1124 with a delivery point 1126. Delivery tubes 1120 may each include a delivery lumen 1125. Alternatively, one or more delivery tubes 1120 may be solid instead of hollow.

Delivery device 1100 also includes a balloon 1130 slidably coupled within catheter 1110 at a center of delivery tubes 1120. Balloon 1130 is not coupled to delivery tubes 1120. Balloon 1130 may be inflated and deflated through an inflation lumen 1135. When inflated, balloon 1130 may anchor distal end 1114 of catheter 1110 within vessel V.

Delivery tubes 1120 may be made of a shape-memory and super-elastic alloy such as nickel titanium, stainless steel, or other suitable materials of sufficient strength and toughness to achieve a desired depth of penetration. Delivery points 1126 may be sharp. Delivery lumens 1125 may have inner surfaces that are coated or treated with polyethylene or other suitable material to reduce the loss or degradation of agents from adhesion inside delivery lumens 1125.

Delivery tubes 1120 are delivered retracted inside catheter 1110, with delivery points 1126 unexposed. Delivery tubes 1120 are positioned in a vessel V at the longitudinal position of a target site T. Catheter 1110 may also be rotated to position delivery points 1126 at a radial position of target site T. Delivery tubes 1120 are then extended from catheter 1110 to expose delivery points 1126. Balloon 1130 is then extended from catheter 1110 distally to delivery tubes 1120, and inflated through inflation lumen 1135 to urge delivery points 1126 toward wall W. Delivery tubes 1120 may continue to be extended to further urge delivery toward wall W and into wall W. Delivery tubes 1120 are extended until delivery points 1126 are positioned at depths of target sites T. Delivery tubes 1120 then deliver an agent through delivery lumens 1125 to target sites T. Alternatively, delivery points 1126 may be treated or coated with an agent which is capable of being absorbed by target sites T.

Figure 3F:
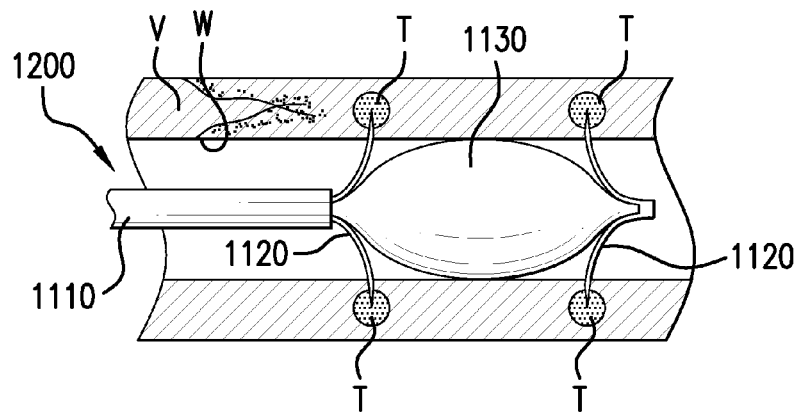

FIG. 3F shows one embodiment of a delivery device 1200. Delivery device 1200 is similar to delivery device 1110, but also includes a plurality of delivery tubes 1120 both proximally and distally to balloon 1130.

Figure 3G:
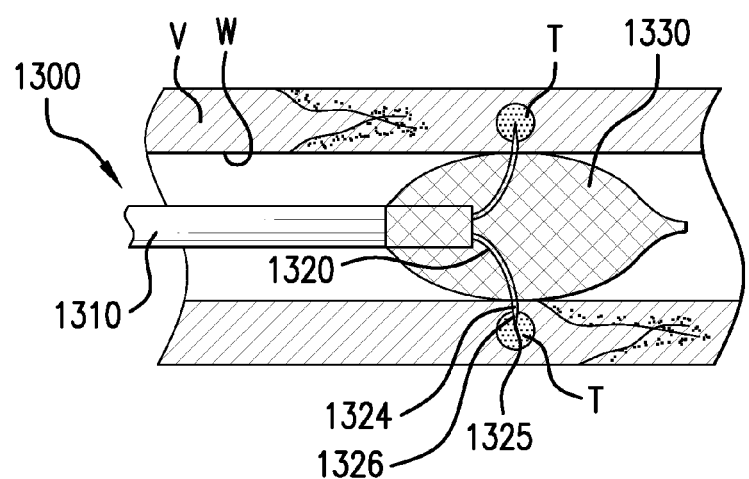

FIG. 3G shows one embodiment of a delivery device 1300. Delivery device 1300 includes a catheter 1310 and a plurality of delivery tubes 1320 slidably coupled within catheter 1310. Delivery tubes 1320 each include a distal end 1324 with a delivery point 1326. Delivery tubes 1320 may each include a delivery lumen 1325. Alternatively, one or more delivery tubes 1320 may be solid instead of hollow.

Delivery device 1300 also includes a positioning device 1330 slidably coupled within catheter 1310. Positioning device 1330 may be a self-expanding structure with an open mesh-like architecture.

Delivery tubes 1320 may be made of a shape-memory and super-elastic alloy such as nickel titanium, stainless steel, or other suitable materials of sufficient strength and toughness to achieve a desired depth of penetration. Delivery points 1326 may be sharp. Delivery lumens 1325 may have inner surfaces that are coated or treated with polyethylene or other suitable material to reduce the loss or degradation of agents from adhesion inside delivery lumens 1325.

Delivery tubes 1320 are delivered retracted inside catheter 1310, with delivery points 1326 unexposed. Delivery tubes 1320 are positioned in a vessel V at the longitudinal position of a target site T. Catheter 1310 may also be rotated to position delivery points 1326 at a radial position of target site T. Positioning structure 1330 is delivered in an unexpanded state inside catheter 1310. Positioning structure 1330 is extended from catheter 1310 and allowed to expand, anchoring distal end 1314 of catheter 1310 within vessel V. Delivery tubes 1320 are then extended from catheter 1310 to expose delivery points 1326 and pass through positioning structure 1330 to penetrate into wall W. Delivery tubes 1320 are extended until delivery points 1326 are positioned at depths of target sites T. Delivery tubes 1320 then deliver an agent through delivery lumens 1325 to target sites T. Alternatively, delivery points 1326 may be treated or coated with an agent which is capable of being absorbed by target sites T.

Positioning device 1330 and delivery points 1326 may be retracted, advanced further and repositioned inside the artery for additional delivery of agent along several locations along the renal artery.

Figure 4A:
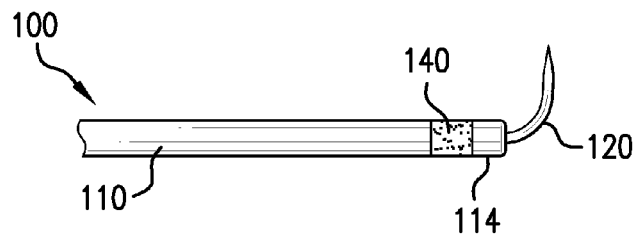
FIG. 4A shows a delivery device with a radioopaque marker.

FIG. 4A shows delivery device 100 with a radioopaque marker 140 coupled to distal end 114 of catheter 110. Radioopaque marker 140 acts as an aid in positioning delivery tube 120. Radioopaque marker 140 may be made of gold, platinum, platinum iridium alloys, or other suitable material.

Figure 4B:
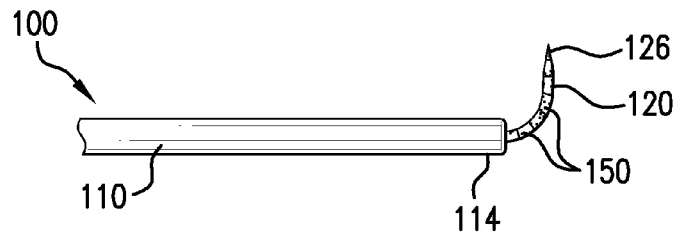
FIG. 4B shows a delivery device with depth markings

FIG. 4B shows delivery device 100 with radioopaque depth markings 150 on delivery tube 120. Depth markings 150 aid in measuring the depth of penetration while guiding delivery point 126 of delivery tube 120 to target site T. Delivery tube 120 may also house a strain gage or other suitable force transducer or sensor to monitor contact with wall W and depth of penetration.

Figure 4C:
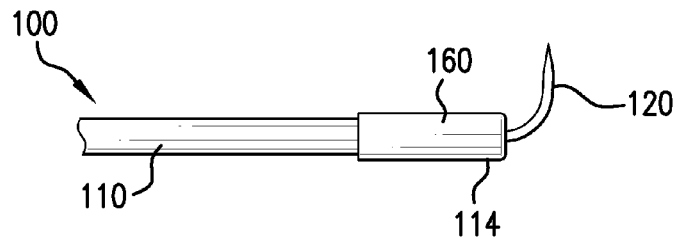
FIG. 4C shows a delivery device with an ultrasound transducer.

FIG. 4C shows delivery device 100 with an ultrasound transducer 160 coupled to distal end 114 of catheter 110. Ultrasound transducer 160 allows imaging of the location and monitoring of the location and depth of delivery tube 120, as well as the volume of agent delivered. Ultrasound-based imaging of the target location may be enhanced by the use of contrast media (contrast-enhanced ultrasound) such as gas-filled microbubbles that are administered intravenously to the systemic circulation prior to the procedure. Further, these gas-filled microbubbles may also be targeted with ligands that bind certain molecular markers that are expressed by the area of imaging interest. Contrast media is injected systemically in a small bolus and detection of bound microbubbles show the area of interest or identify particular cells in the area of interest.

Figure 4D:
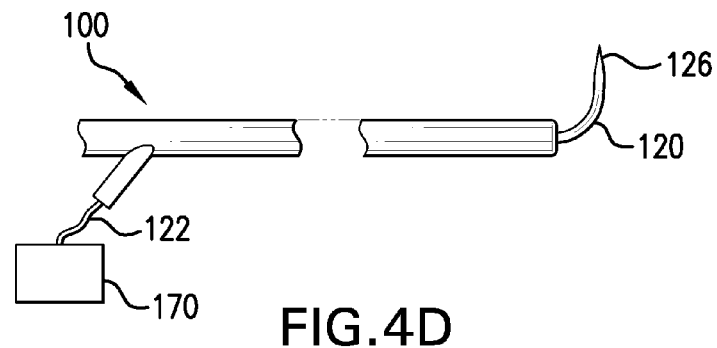
FIG. 4D shows a delivery device with an ultrasound device.

FIG. 4D shows delivery device 100 with an ultrasound device 170 coupled to a proximal end 122 of delivery tube 120. Ultrasound device 170 transmits ultrasound energy through delivery tube 120 to delivery point 126, which may enhance the bioavailability of the agent.

Figure 4E:
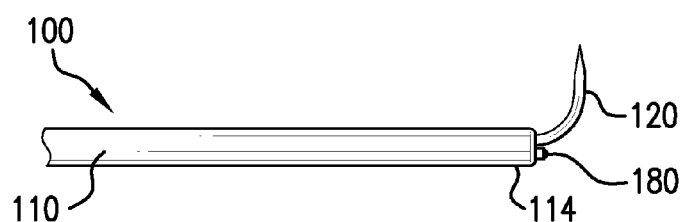
FIG. 4E shows a delivery device with a visualization device.

FIG. 4E shows delivery device 100 with a visualization device 180 coupled to distal end 114 of catheter 110. Visualization device 180 allows direct visualization of delivery tube 120 and wall W. Visualization device 180 may be electromagnetic transducer, magnetic-resonance imaging (MRI) transducer, angioscope, camera, or other suitable device.

Visualization device 180 may be an electromagnetic transducer, including one or more electrode pairs, coupled to distal end 114 of catheter 110. The electromagnetic transducer works in conjunction with a low-level magnetic field ($5 \times 10^{-6}$ to $5 \times 10^{-5}$ Tesla) generated by electromagnetic coils placed on the operating table beneath the patient. The electromagnetic transducer can be moved along the vessel to record and map the electrical activity along the entire surface of the renal artery. These electrical signals map the neuron activity or electrical conduction pathways of the peripheral nervous system surrounding the renal arteries, and aid in identifying the target location for delivering the agent.

Visualization device 180 may be a magnetic-resonance imaging (MRI) transducer coupled to distal end 114 of catheter 110. The MRI transducer works in conjunction with a specific contrast agent delivered, as a bolus, to the patient to assist in imaging the electrical conduction of the peripheral nervous system surrounding the renal arteries, and to help in identifying the target site for denervation.

Figure 4F:
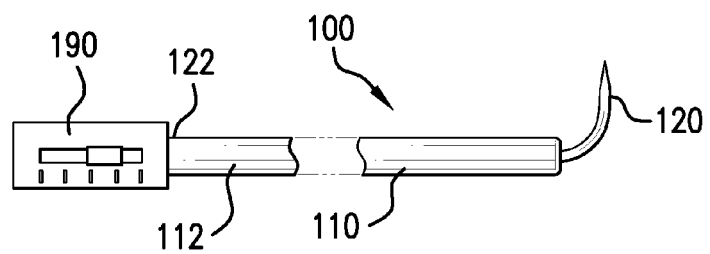
FIG. 4F shows a delivery device with a depth control.

FIG. 4F shows delivery device 100 with a depth control 190 coupled to proximal end 112 of catheter 110 and proximal end 122 of delivery tube 120. Depth control 190 includes marks which indicate how far delivery tube 120 has been extended.

Delivery device 100 may include a separate luminal port in the catheter to inject radioopaque contrast agents to image the location of the catheter and the target site using X-ray fluoroscopy or angiography during the procedure.

Figure 5A:
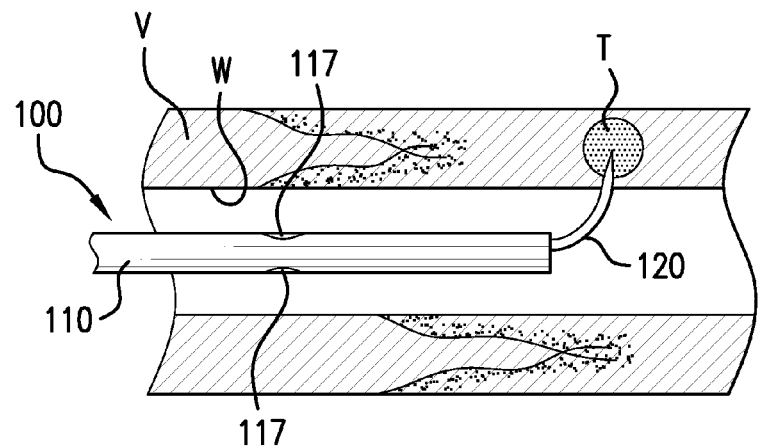
FIG. 5A shows a delivery device with flush ports.

FIG. 5A shows delivery device 100 having a catheter 110 with flush ports 117. Flush ports 117 may introduce a neutralizing substance into vessel V which neutralizes at least some of the agent delivered by delivery tube 120 which leaks back into vessel V.

Figure 5B:
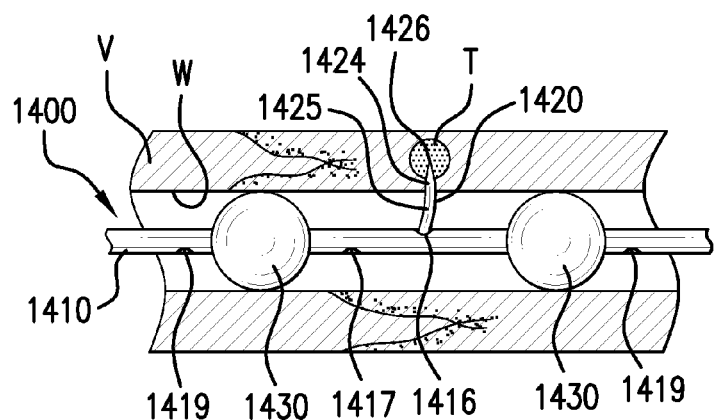
FIG. 5B shows a delivery device with dual balloons.

FIG. 5B shows one embodiment of a delivery device 1400. Delivery device 1400 includes a catheter 1410 with a delivery tube port 1416 and an aspiration port 1417. Delivery device 1400 also includes a delivery tube 1420 slidably coupled within catheter 1410. Delivery tube 1420 includes a distal end 1424 with a delivery point 1426. Delivery tube 1420 may also include a delivery lumen 1425. Alternatively, delivery tube 1420 may be solid instead of hollow. Delivery device 1400 also includes balloons 1430 coupled to catheter 1410 both proximally and distally to delivery tube port 1416 and aspiration port 1417. Catheter 1410 includes perfusion ports 1419 distal and proximal to balloons 1430.

Delivery tube 1420 is outwardly biased from a longitudinal axis of catheter 1410. Delivery tube 1420 may be made of a shape-memory alloy such as nickel titanium, or other suitable material. Delivery tube 1420 may be preshaped to a desired three-dimensional configuration, using shape-memory or super-elastic properties of nickel-titanium or spring properties of steels or other alloys used to make springs, so that once the catheter is retracted, delivery tube 1420 makes contact with and penetrates into wall W. Delivery point 1426 may be sharp. Delivery lumen 1425 may have an inner surface that is coated or treated with polyethylene or other suitable material to reduce the loss or degradation of agents from adhesion inside delivery lumen 1425.

Delivery tube 1420 is delivered retracted inside catheter 1410, with delivery point 1426 unexposed. Delivery tube 1420 is positioned in a vessel V at the longitudinal position of a target site T. Catheter 1410 may also be rotated to position delivery point 1426 at a radial position of target site T. Balloons 1430 are inflated to anchor the catheter in vessel V and to isolate a portion of vessel V. Delivery tube 1420 is then extended from catheter 1410 through delivery tube port 1416 to expose delivery point 1426 and penetrate into wall W. Delivery tube 1420 is extended until delivery point 1426 is positioned at a depth of target site T. Delivery tube 1420 then delivers an agent through delivery lumen 1425 to target site T. Alternatively, delivery point 1426 may be treated or coated with an agent which is capable of being absorbed by target site T. Excess agent which returns into vessel V is isolated by balloons 1430 and may be vented out through aspiration port 1417. Perfusion ports 1419 allow fluid flow through vessel V to continue even when balloons 1430 are inflated.

Figure 6:
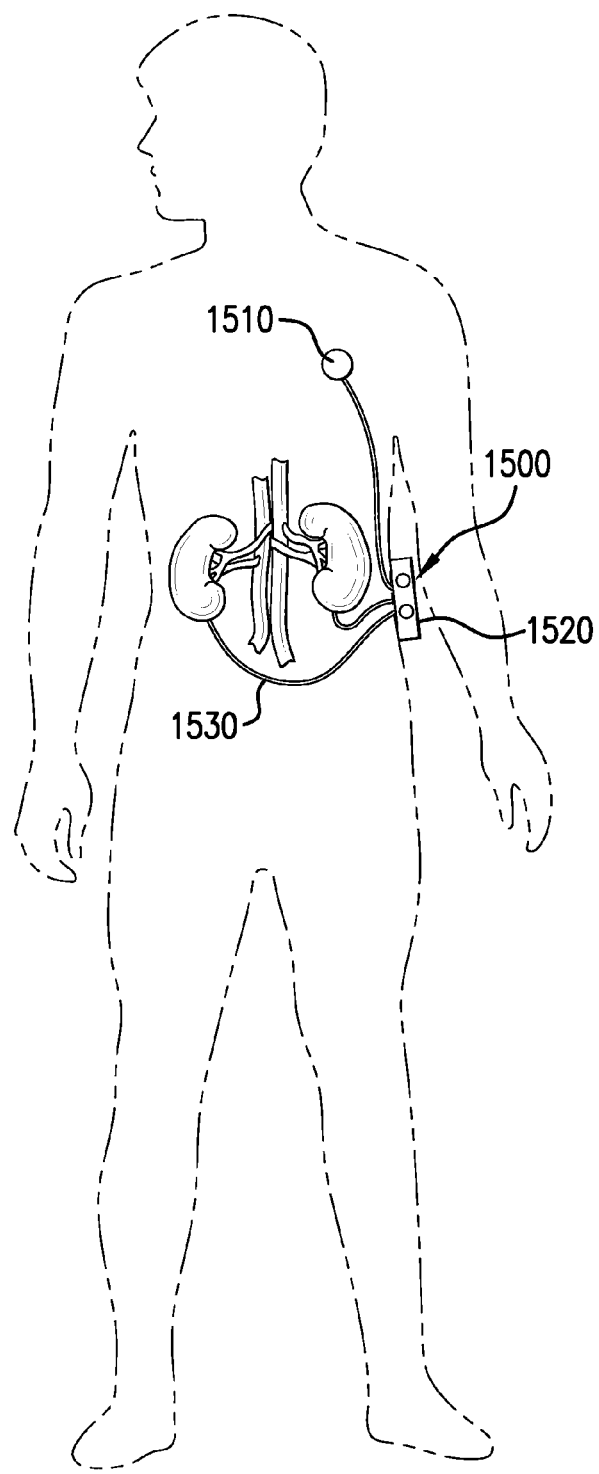
FIG. 6 shows a delivery system with a closed-feedback loop.

FIG. 6 shows one embodiment of a delivery device 1500. Delivery device 1500 includes a sensor 1510 coupled to a pump 1520 and a catheter 1530. Sensor 1510 is configured to measure a physiological parameter. Pump 1520 includes control software and an agent. Catheter 1530 is implanted in a suitable location within the body. Pump 1520 receives data from sensor 1510, and responds by using control software to determine an amount of the agent to deliver through catheter 1530. For example, sensor 1510 may be used to measure blood pressure, which pump 1520 uses to determine an amount of a denerving agent to deliver through the catheter 1530, which is implanted to deliver the agent to the renal nerves. Delivery device 1500 thus uses a closed feedback loop to control a physiological parameter such as blood pressure.

Figure 7A:
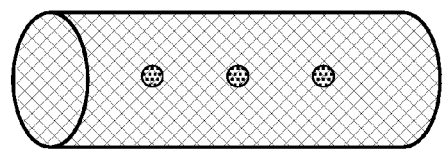
FIG. 7A shows a drug-eluting stent.
Figure 7B:
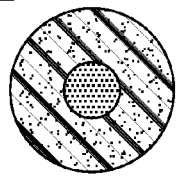
FIG. 7B shows a time-release agent.

FIG. 7A shows a drug-eluting stent 1600 which may be implanted in a renal artery. FIG. 7B shows a polymer-encapsulated time-release agent 1700.

FIGS. 8A-8I show one embodiment of a method of using a delivery device 100.

Figure 8A:
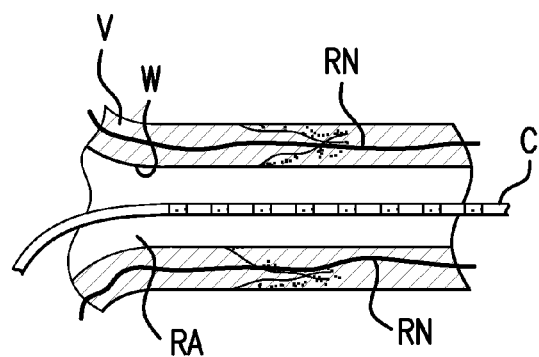
FIGS. 8A-8I show one embodiment of a method for using delivery device 100.

FIG. 8A shows mapping of vessel V and nerves using a mapping catheter C. Mapping catheter C is introduced into vessel V and used to locate and map the nerves surrounding vessel V. In this example, vessel V is a renal artery and the nerves are renal nerves. Alternatively, vessel V may be a renal vein or other vessel which provides access to the renal nerves. Mapping catheter C may be an electrical mapping catheter, an ultrasound catheter, a magnetic resonance imaging (MRI) catheter, or other suitable catheter. An electrical mapping catheter may be cardiac mapping catheter adapted for use in the renal artery and renal nerves. An ultrasound catheter may be used with contrast agents such as paramagnetic (e.g., gadolinium, manganese) and superparamagnetic (e.g., iron oxide) contrast agents, in the form of nanoparticles or other suitable form. An MRI catheter may be used with fluorescent nanospheres, fluorescent microspheres and other agents to enhance imaging.

Figure 8B:
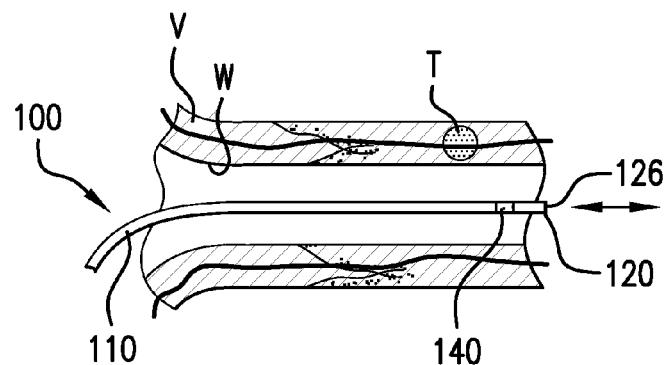

FIG. 8B shows introducing delivery device 100 into vessel V. Catheter 110 may be moved along vessel V to place delivery point 126 of delivery tube 120 at the longitudinal position of target site T. Catheter 110 is capable of being placed in the proximal third of the renal artery beginning at the aorto-ostial junction of the aorta and renal artery. Catheter 110 may be placed with the assistance of radioopaque marker 140.

Figure 8C:
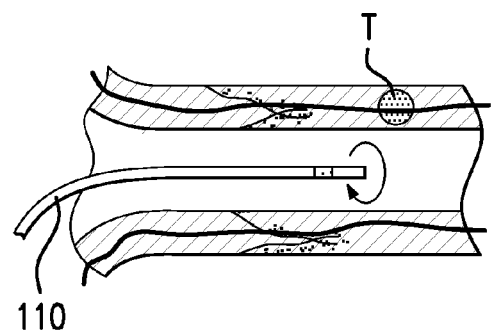

FIG. 8C shows rotating catheter 110 in vessel V to place delivery tube 120 at the radial position of target site T.

Figure 8D:
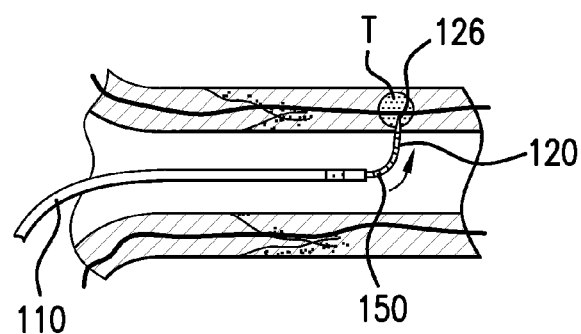

FIG. 8D shows extending delivery tube 120 from catheter 110 to penetrate into wall W of vessel V. Delivery tube 120 is extended until delivery point 126 is placed at the depth of target site T. Delivery point 126 may be placed at target site T with the assistance of depth markings 150, ultrasound transducer 160, or other suitable features and devices. Depth control 190 may be used to control delivery tube 120 and delivery point 126. In renal arteries, the depth for healthy vessels may have a range of 1-10 mm, with a typical range of 2-3 mm. For diseased vessels, such as those lined with atherosclerotic plaque, the depth may have a range of 3-15 mm, with a typical range of 4-7 mm.

Figure 8E:
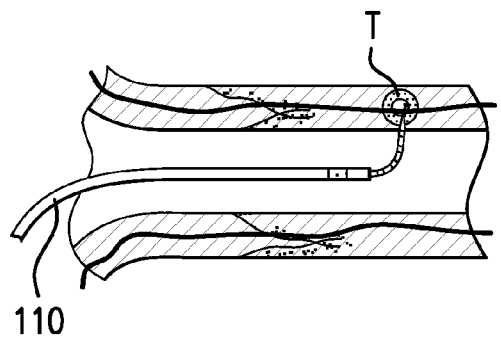

FIG. 8E shows delivering a preparatory agent to target site T using delivery tube 120. Preparatory agent may be an anesthetic, vasoconstrictor, vasodilator, neurotropic agent conjugated to a traceable marker, steroid, or other suitable agent. Preparatory agent serves to anesthesize, reduce uptake of delivered agents by vessel V, and other purposes. The traceable marker may be a lipophilic dye or fluorophore (e.g., nile red, long-chain carbocyanines), a radioisotope (e.g., thallium 201Ti, technetium 99 mTC, gallium 67Ga, lithium 6Li, lithium 7Li), metallic nanoparticles (e.g., gadolinium, iron oxide, manganese), an enzyme, contrast agents (e.g., godadiamide), and/or antibodies (e.g., antibodies against myelin oligodendrocyte glycoprotein, axonin-1, neuronal cell adhesion molecule, neuroglial cell adhesion molecule).

Figure 8F:
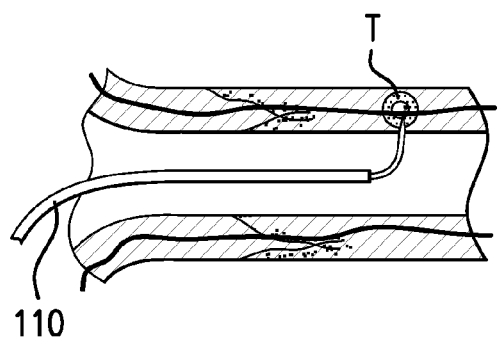

FIG. 8F shows delivering a priming agent to target site T using delivery tube 120. Delivering a priming agent may be performed at a controlled rate. A priming agent may be used as an initial signal to activate or inactivate nerve intracellular signaling, nerve cell action potential, or nerve cell membrane repolarization.

Priming agent may be an inotropic drug (e.g., cardiac glycoside, hoiamides), channel blocker (e.g., conotoxins, amlodipine, diltiazem, verapamil), excitatory amino acid (e.g., glutamate, domoic acid), beta-blocker (e.g., propranolol), bi-partite fusion construct, pro-apoptotic factor (e.g., staurosporine, tumor necrosis factor (TNF), antibody against nerve growth factor receptor p75, glucocorticoid), neurotropic agent conjugated to a neuroactive agent, or anti-manic agent (e.g., lithium).

Neurotropic agents may be an antibody against UCHL1, myelin oligodendrocyte glycoprotein, axonin-1, neuronal cell adhesion molecule, neuroglial cell adhesion molecule; nerve growth factor, reovirus σ1 protein, rabies spike glycoprotein, Theiler's murine encephalomyelitis virus (TMEV), or other suitable agents used to bind to the surface of nerve cells in a specific manner.

Priming agent may also be a toxin or toxic peptide (e.g., conotoxin, tetrodotoxin, saxitoxin), alcohol (e.g., ethanol), an enzyme (e.g., eosinophil cationic protein/RNase 3), phenol, or an anti-convulsant (carbamazepine).

Priming agent may also be a neurotropic agent (e.g., ciliary neurotropic factor (CNTF), brain derived neurotropic factor (BDNF), glial derived nexin (GDN)).

Priming agent may also be batrachotoxin, neosaxitoxin, gonyautoxins, aurotoxin, agitoxin, charybdotoxin, margaoxin, slotoxin, scyllatoxin, hefutoxin, calciseptine, taicatoxin, calcicludine, PhTx3, amphetamine, methamphetamine, or MDMA.

Figure 8G:
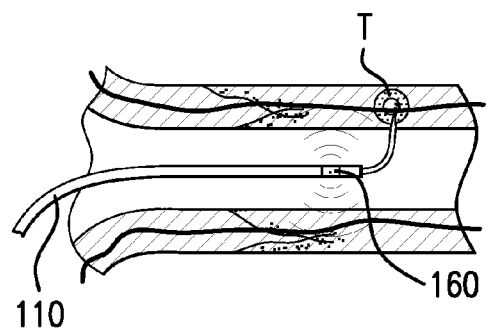

FIG. 8G shows an optional step of enhancing delivery of an agent using ultrasound device 170. Alternatively, enhancing delivery may be performed with mechanical, ultrasonic, thermal, and/or other energy means.

Figure 8H:
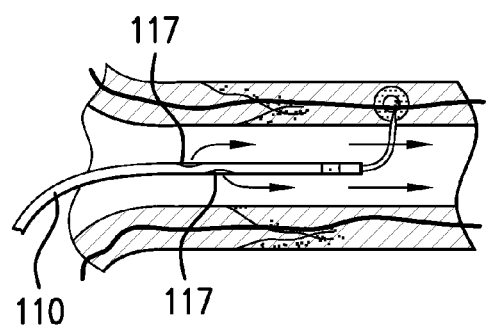

FIG. 8H shows an optional step of delivering a neutralizing agent using flush ports 117 in catheter 110. Neutralizing agent deactivates at least some of any excess agent which may escape back into vessel V or excess agent that remains unbound to nerve cells. Neutralizing agent may be a dilutant such as saline, a neutralizing antibody (e.g., digoxin immune Fab), an enzyme (e.g., glutamate dehydrogenase), sodium bicarbonate (to neutralize phenol), a chelating agent (e.g., EDTA, EGTA), a steroid, non-steroidal anti-inflammatory drugs (e.g., aspirin, ibuprofen, sirolimus), or other suitable agent.

Figure 8I:
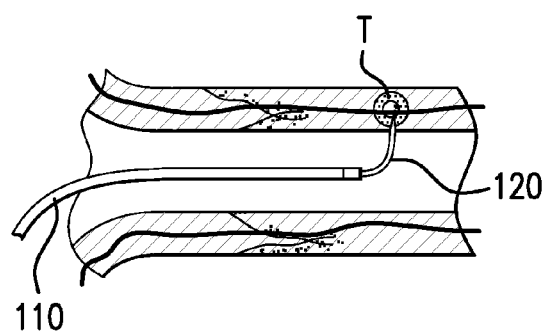

FIG. 8I shows delivering a secondary agent to target site T using delivery tube 120. Secondary agent may be delivered at a controlled rate. Secondary agent may be delivered at the same time as priming agent, or at some predetermined time after priming agent. Priming agent and secondary agent may be different agents. Priming agent and secondary agent may also be the same agent, in the same or different volumes and/or concentrations. Priming agent and secondary agent may be different agents and may be linked together to form a bi-partite construct. Priming agent may also be linked to two different secondary agents to form a tri-partite construct. The function of sequential or combined delivery of priming and secondary agents is to deliver multiple stimuli to the nerve cell to promote or induce nerve cell death.

The use of a priming agent and a secondary agent may result in a synergistic effect. This synergistic effect may result in (1) smaller amounts of the agents needed than if either agent was used by itself, (2) faster action than if either agent was used by itself, and (3) greater effectiveness than if either agent was used by itself.

Some or all of the method may be repeated as desired. For example, delivering a secondary agent may be followed by enhancing delivery and delivering a neutralizing agent. As another example, delivering a secondary agent may be followed by delivering another secondary agent.

FIGS. 9A-9F show one embodiment of a method for using delivery device 1000.

Figure 9A:
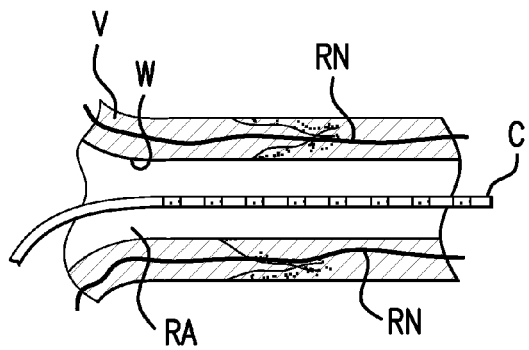
FIGS. 9A-9F show one embodiment of a method for using delivery device 1000.

FIG. 9A shows mapping of vessel V and nerves using a mapping catheter C. Mapping catheter C is introduced into vessel V and used to locate and map the nerves surrounding vessel V. In this example, vessel V is a renal artery and the nerves are renal nerves. Alternatively, vessel V may be a renal vein or other vessel which provides access to the renal nerves. Mapping catheter C may be an electrical mapping catheter, an ultrasound catheter, a magnetic resonance imaging (MRI) catheter, or other suitable catheter.

Figure 9B:
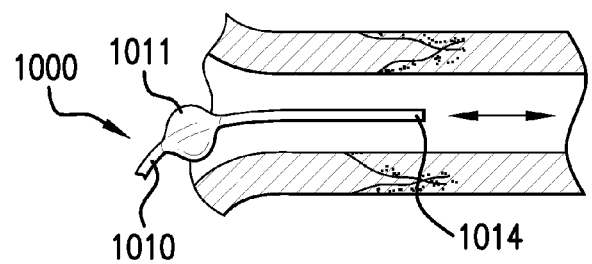

FIG. 9B shows introducing delivery device 1000 into vessel V. Catheter 1010 may be moved along vessel V to place distal end 1014 at the longitudinal position of target sites T. Catheter 1010 is capable of being placed in the proximal third of the renal artery beginning at the aorto-ostial junction of the aorta and renal artery. Catheter 1010 may be placed with the assistance of a positioning element 1011 such as a balloon or self-expanding structure. Positioning element 1011 is coupled to catheter 1010 at a fixed or known distance from distal end 1014. Positioning element 1011 may be configured to fit at the ostium of the renal artery.

Figure 9C:
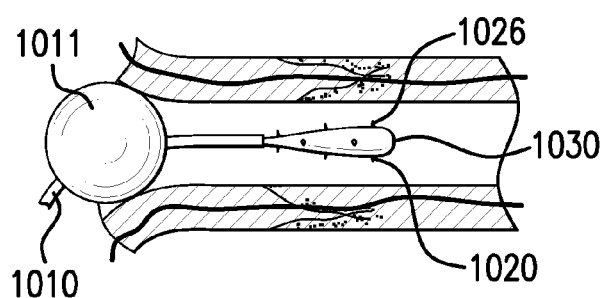

FIG. 9C shows deploying balloon 1030 from catheter 1010. Positioning element 1011 is fully expanded, and may be seated at the ostium of the renal artery, thus positioning distal end 1014 and balloon 1030 at a fixed or known distance from the ostium of the renal artery.

Figure 9D:
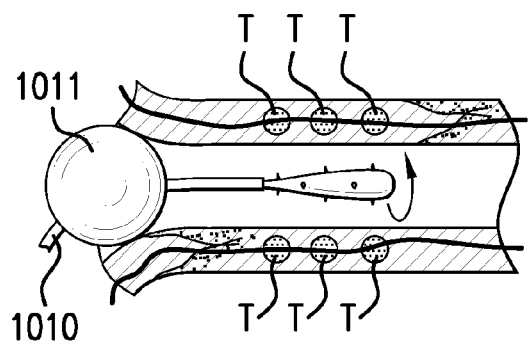

FIG. 9D shows rotating balloon 1030 in vessel V to place delivery points 1026 of balloon 1030 at the radial positions of target sites T.

Figure 9E:
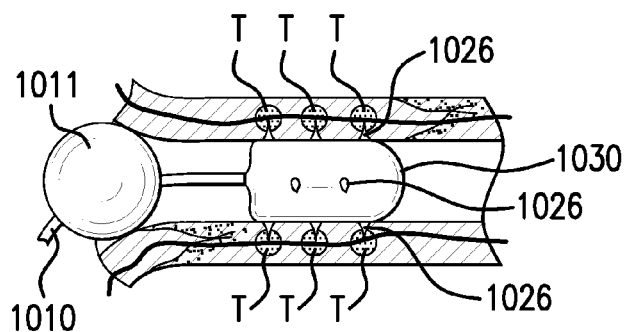

FIG. 9E shows expanding balloon 1030 in vessel V to urge delivery points 1026 into wall W of vessel V. Delivery points 1026 are of a known length, and penetrate a known distance into wall W to reach target sites T. Delivery points 1026 may have different lengths and configurations. For example, delivery points 1026 may become have lengths that become shorter with distance from the ostium of the renal artery. As another example, delivery points 1026 may have delivery lumens 1025 that become smaller and deliver less agent with distance from the ostium of the renal artery.

Delivery points 1026 may be arranged in a predetermined configuration or pattern. The configuration or pattern of delivery points 1026 may be selected to maximize the probability they will be positioned on or near the renal nerves in the renal artery, based on distribution data for the renal nerves. Several different preconfigured patterns may be available, with selection based on results of mapping of the renal nerves. The configuration or pattern of delivery points 1026 may also be selected to be non-circumferential to reduce the effects of any swelling or stenosis. For example, the configuration or pattern may be a helical or spiral pattern, as opposed to one or more circumferential rings.

Delivery points 1026 are capable of creating noncontiguous or discrete delivery areas. Delivery points 1026 are capable of delivering very small quantities of agents. The ability to deliver very small quantities in a very focused and targeted manner allows for a greater selection of very toxic agents to be used.

Figure 9F:
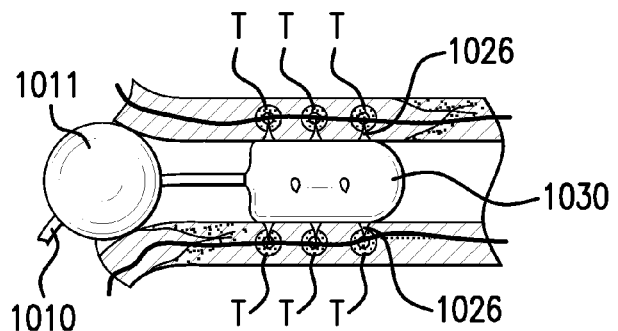
Figure 10A:
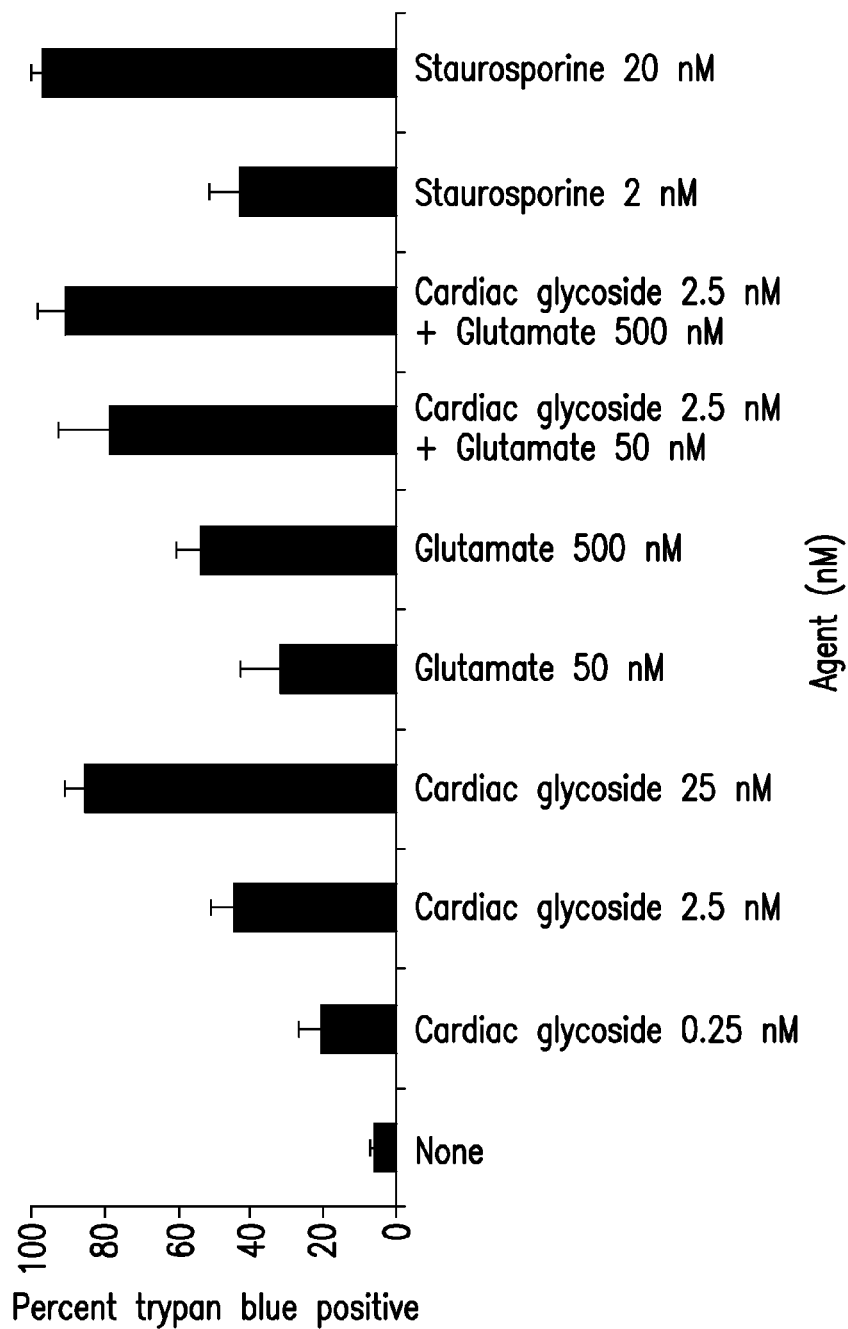
FIG. 10A shows the amount of cell death caused by several of agents for a fixed amount of time.
Figure 10B:
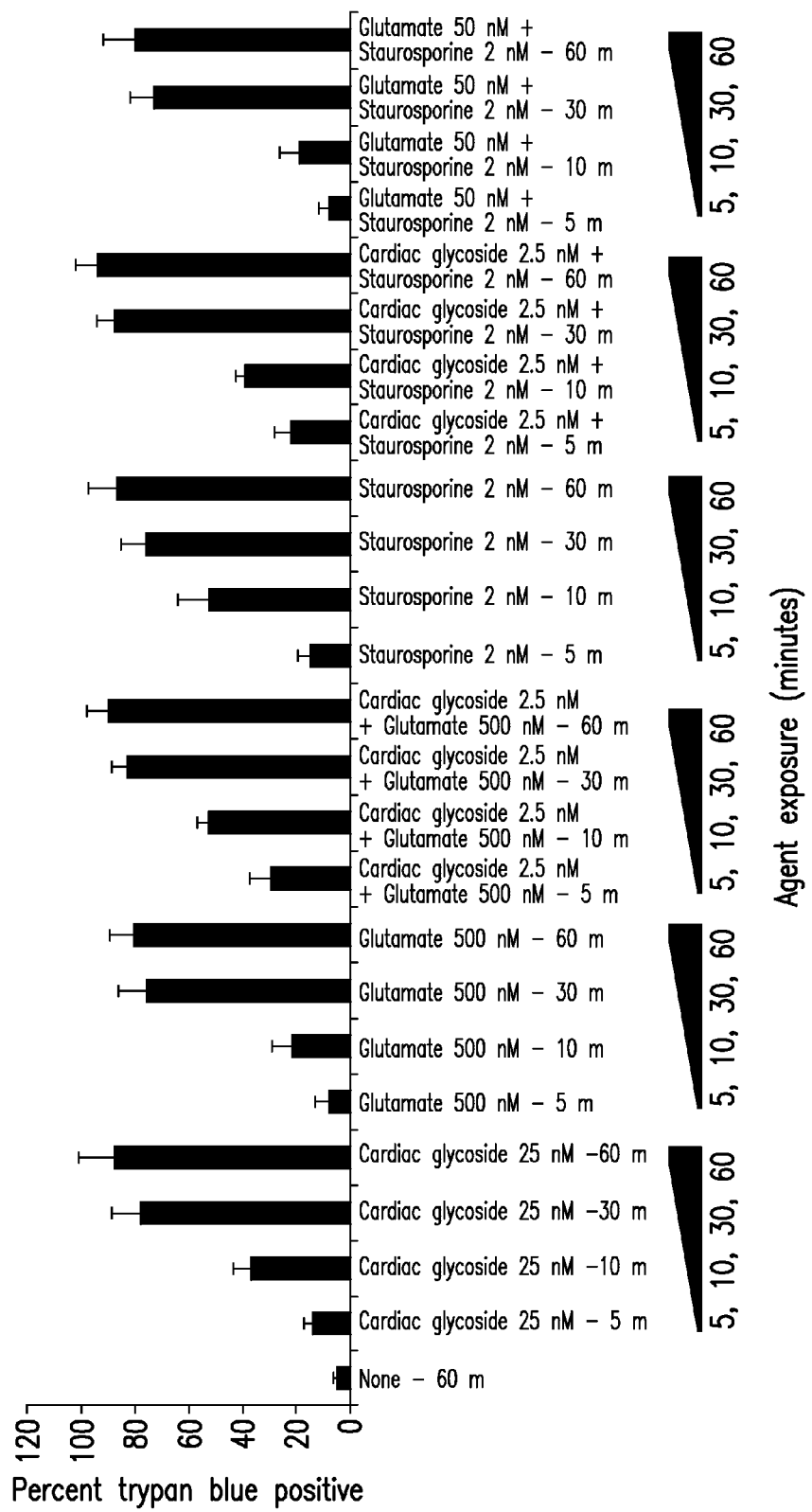
FIG. 10B shows the amount of cell death caused by several agents versus time.

FIG. 9F shows delivering an agent to target sites T. Agent may be one or more agents, delivered sequentially or substantially simultaneously.

Other methods may be used to deliver agents. For example, agents may be delivered with a drug-eluting stent. The stent may be configured to fit inside the renal artery, and may be bioabsorbable. The stent may be configured to deliver a priming agent during a first period of time, and a secondary agent during a second period of time. As another example, agents may be delivered in time-release formulations, such as encapsulated in polymers. The time-release formulations may be configured to release a priming agent during a first period of time, and a secondary agent during a second period of time. As yet another example, agents may be delivered with microbubbles having a diameter of approximately 1-10 micrometers, used in combination with focused ultrasound. These microbubbles may temporarily permeabilize the vessel wall in a localized area to permit the passage of neuroactive or neurotoxic agents through the vasculature and to the surrounding interstitial tissue near a nerve cell.

Agents may be transiently housed within or complexed with liposomes. The liposomes may contain nerve growth factor (NGF) on the outer leaflet of the liposomal membrane or may contain one or more other neurotropic agent (e.g., ciliary neurotropic factor (CNTF), brain derived neurotropic factor (BDNF), glial derived nexin (GDN)).

Glutamate or domoic acid (0.00005-700 mM) can be administered as a denerving agent singly or in combination. Excessive stimulation of neurons by glutamate initiates a cascade of ion fluxes, cellular swelling and death in nerve cells. Additionally, fibroblasts expressing human NR1a/2A or NR1a/2B NMDA receptors are hypersensitive to glutamate receptor-mediated toxicity and NR1a/2B NMDA receptors are expressed in tissues outside of the brain (kidney, adrenal cortex, pancreas, heart and others) in low amounts.

L-glutamate is the major excitatory neurotransmitter in the central nervous system and activates both inotropic and metabotropic glutamate receptors. Glutamatergic neurotransmission is involved in most aspects of normal brain function and can be perturbed in many neuropathologic conditions. The metabotropic glutamate receptors are a family of G protein-coupled receptors that have been divided into 3 groups on the basis of sequence homology, putative signal transduction mechanisms, and pharmacologic properties. Group I includes GRM1 and GRM5 and these receptors have been shown to activate phospholipase C. Group II includes GRM2 and GRM3 while Group III includes GRM4, GRM6, GRM7 and GRM8.

Group II and III receptors are linked to the inhibition of the cyclic AMP cascade but differ in their agonist selectivities. The canonical alpha isoform of the metabotropic glutamate receptor 1 gene is a disulfide-linked homodimer whose activity is mediated by a G-protein-coupled phosphatidylinositol calcium second messenger system. GRM receptor expression is not exclusive to neurons and has been determined to be present in kidney, liver, heart, lungs, thyroid and other organs.

Cardiac glycosides are inotropic drugs that specifically inhibit Na+,K(+) ATPase activity. Cardiac glycoside binding to the alpha subunit of the Na+,K(+) ATPase induces intracellular ion flux. Extended inhibition of Na+,K(+) ATPase function can induce apoptosis in nerve cells. Additionally, brief exposure (5 to 10 minutes) to high concentrations of cardiac glycoside (1-10 mM) is toxic to nerve cells.

A combination of an amino acid and an inotropic drug can be administered to potentiate nerve cell blockade, sensitivity, damage or death. Exposure to cardiac glycoside (0.01-1 mM)

prior to exposure of a nerve cell to glutamate produces supersensitivity in a nerve cell and induces glutamate excitotoxicity.

Ziconotide is a synthetic peptide derived from a toxin produced by the marine snail, *Conus magus*. Ziconotide selectively targets N-type voltage-gated calcium channels. Additionally, other members of the cysteine-rich conotoxin superfamily can be used to target nerve cells. Conotoxins and peptides derived from conotoxins (conopeptides) have also shown efficacy in clinical applications. Targeted administration of a high concentration of toxic peptide can induce nerve cell damage and death.

Hoiamide B(2) is a cyclic depsipeptide produced by marine cyanobacteria. The linear lipopeptide, hoiamide C(3) is also produced by marine cyanobacteria. Both metabolites possess the unique hoiamide structural class, characterized by an acetate extended and S-adenosyl methionine modified isoleucine, a central tri-heterocyclic core of two alpha-methylated thiazolines and one thiazole, and a highly oxygenated and methylated C-15 polyketide unit. Hoiamides have been demonstrated to induce sodium influx and suppress calcium oscillations.

Eosinophil cationic protein/RNase 3 can induce neurotoxicity, consistent with apoptosis, in a dose-dependent manner. Upon binding to the nerve cell surface, an increase in free cytosolic calcium flux, induction of caspase-3, -8, and -9 can be observed.

The bi-partite fusion construct contains (i) a neurotropic agent that has high affinity to one or more receptors on the surface of a nerve cell, and is linked by a flexible linker to (ii) a neuroactive agent that alters a nerve cell. In one example, the neurotropic agent is the β-subunit of nerve growth factor (NGF). NGF is internalized into the neurons following binding to cognate receptors located on nerve cells.

A bi-partite neurotropic fusion construct may be used to mark nerve cells and nerve bundles. The neurotropic agent can be a protein, peptide or other ligand for a receptor located on the surface of nerve cell. The neurotropic agent is linked by a hydrolysable or flexible linker (protein, PEGylated crosslinker, or other) to a traceable marker. The traceable marker can be a fluorophore, radioisotope, metallic nanoparticles, enzyme, antibody or other and can be detected by conventional methods. Binding of the neurotropic agent delivers the traceable marker to the nerve cell. The binding of the fusion construct labels the outside and inside of the nerve (upon internalization).

A bi-partite neurotropic fusion construct to generate nerve cell blockade, damage or death. The neurotropic agent can be a protein, peptide or other ligand for a receptor located on the surface of nerve cell. The neurotropic agent is linked by a hydrolysable or flexible linker (protein, PEGylated crosslinker, or other) to a neuroactive agent. The neuroactive agent can be a toxin, drug, hoiamide, antibody or other and can interrupt nerve cell homeostasis. Binding of the neurotropic agent delivers the neuroactive agent to the nerve cell. The binding of both agents potentiates the action of the neuroactive agent.

MDMA, also known as ecstasy, is an amphetamine-like stimulant known to induce apoptotic damage of serotonergic nerves.

Calcium channel blockers block voltage-gated calcium channels to decrease the electrical conductance of a nerve cell and are used as anti-epileptic drugs. Targeted administration of a high concentration of calcium channel blocker can induce nerve cell damage and death.

Potassium channel blockers block potassium channels to prolong repolarization of the nerve cell and are used as anti-arrhythmic drugs. Targeted administration of a high concentration of potassium channel blocker can induce nerve cell damage and death.

Pro-apoptotic factors activate the caspase signaling cascade, leading to a "quiet" programmed cell death characterized by blebbing, loss of cell membrane asymmetry and attachment, cell shrinkage, nuclear fragmentation, chromatin condensation, and chromosomal DNA fragmentation. This is separate from necrosis, which is traumatic cell death that results from physical, electrical or chemical trauma and is pro-inflammatory.

EXAMPLE 1

A vasoconstrictor (antidiuretic hormone (ADH or vasopressin) or tetrahydrozoline) is first administered to vessels surrounding the target site to minimize leakage of the priming or secondary agents.

A priming agent of digoxin at a concentration of 0.0001-10 mM in a volume of 0.05-2 cc is then administered at a nerve proximal site to prime the neurons by inhibiting the transport of potassium and sodium across the nerve cell membrane and subsequently inducing an intracellular calcium flux.

Approximately 0.1-20 minutes later, a secondary agent of glutamate at a concentration of 0.1-700 mM in a volume of 0.05-2 cc is then administered at a nerve proximal site to induce neuronal excitotoxicity.

Vasoconstriction results from the increased concentration of calcium (Ca2+ ions) within vascular smooth muscle cells. However, the specific mechanisms for generating an increased intracellular concentration of calcium depends on the vasoconstrictor. Two common stimuli for eliciting smooth muscle contraction are circulating epinephrine and activation of the sympathetic nervous system (through release of norepinephrine) that directly innervates the muscle. These compounds interact with cell surface adrenergic receptors. Such stimuli result in a signal transduction cascade that leads to increased intracellular calcium from the sarcoplasmic reticulum (SR) through IP3 mediated calcium release, as well as enhanced calcium entry across the sarcolemma through calcium channels. The rise in intracellular calcium complexes with calmodulin, which in turn activates myosin light chain kinase. This enzyme is responsible for phosphorylating the light chain of myosin to stimulate cross bridge cycling.

Cardiac glycosides are used therapeutically mainly in the treatment of congestive heart failure. These effects are caused by the ability to increase cardiac output by increasing the force of contraction by increasing intracellular calcium as described below, increasing calcium-induced calcium release and thus contraction. Drugs such as ouabain and digoxin are cardiac glycosides.

Normally, sodium-potassium pumps in the membrane of cells (in this case, cardiac myocytes) pump potassium ions in and sodium ions out. Cardiac glycosides inhibit this pump by stabilizing it in the E2-P transition state, so that sodium cannot be extruded, therefore increasing intracellular sodium concentration. A second membrane ion exchanger, NCX, is responsible for "pumping" calcium ions out of the cell and sodium ions in (3Na/Ca). Raised intracellular sodium levels inhibit this pump, so calcium ions are not extruded and will also begin to build up inside the cell.

Increased cytoplasmic calcium concentrations cause increased calcium uptake into the sarcoplasmic reticulum via the SERCA2 transporter. Raised calcium stores in the SR allow for greater calcium release on stimulation, so the myocyte can achieve faster and more powerful contraction by cross-bridge cycling. The refractory period of the AV node is increased, so cardiac glycosides also function to regulate heart rate.

Binding of cardiac glycoside to Na—K ATPase is slow, and also, after binding, intracellular calcium increases gradually. This can be seen in the delayed action of digitalis, even on IV injection.

Raised extracellular potassium decreases binding of cardiac glycoside to Na—K ATPase, resulting in increased toxicity of these drugs in the presence of hypokalemia.

Digoxin binds to a site on the extracellular aspect of the α-subunit of the Na+/K+ ATPase pump in the membranes of heart cells (myocytes) and decreases its function. This causes an increase in the level of sodium ions in the myocytes, which leads to a rise in the level of intracellular calcium ions. This occurs because of a sodium/calcium exchanger on the plasma membrane, which depends on a constant inward sodium gradient to pump out calcium. Digoxin decreases sodium concentration gradient and the subsequent calcium outflow, thus raising the calcium concentration in myocardiocytes and pacemaker cells.

Increased intracellular calcium lengthens Phase 4 and Phase 0 of the cardiac action potential, which leads to a decrease in heart rate. Increased amounts of Ca2+ also leads to increased storage of calcium in the sarcoplasmic reticulum, causing a corresponding increase in the release of calcium during each action potential. This leads to increased contractility, the force of contraction, of the heart.

There is also evidence that digoxin increases vagal activity, thereby decreasing heart rate by slowing depolarization of pacemaker cells in the AV node. This negative chronotropic effect would therefore be synergistic with the direct effect on cardiac pacemaker cells. Digoxin is used widely in the treatment of various arrhythmias. Glutamate is the most abundant excitatory neurotransmitter in the vertebrate nervous system. At chemical synapses, glutamate is stored in vesicles. Nerve impulses trigger release of glutamate from the pre-synaptic cell. In the opposing post-synaptic cell, glutamate receptors, such as the NMDA receptor, bind glutamate and are activated. Because of its role in synaptic plasticity, glutamate is involved in cognitive functions like learning and memory in the brain. The form of plasticity known as long-term potentiation takes place at glutamatergic synapses in the hippocampus, neocortex, and other parts of the brain. Glutamate works not only as a point-to-point transmitter but also through spill-over synaptic crosstalk between synapses in which summation of glutamate released from a neighboring synapse creates extrasynaptic signaling/volume transmission.

Glutamate transporters are found in neuronal and glial membranes. They rapidly remove glutamate from the extracellular space. In brain injury or disease, they can work in reverse, and excess glutamate can accumulate outside cells. This process causes calcium ions to enter cells via NMDA receptor channels, leading to neuronal damage and eventual cell death, and is called excitotoxicity. The mechanisms of cell death include damage to mitochondria from excessively high intracellular Ca2+, and Glu/Ca2+-mediated promotion of transcription factors for pro-apoptotic genes, or downregulation of transcription factors for anti-apoptotic genes.

Excitotoxicity due to glutamate occurs as part of the ischemic cascade and is associated with stroke and diseases like amyotrophic lateral sclerosis, lathyrism, autism, some forms of mental retardation, and Alzheimer's disease.

Glutamic acid has been implicated in epileptic seizures. Microinjection of glutamic acid into neurons produces spontaneous depolarizations around one second apart, and this firing pattern is similar to what is known as paroxysmal depolarizing shift in epileptic attacks. This change in the resting membrane potential at seizure foci could cause spontaneous opening of voltage-activated calcium channels, leading to glutamic acid release and further depolarization.

EXAMPLE 2

A vasoconstrictor (antidiuretic hormone (ADH or vasopressin) or tetrahydrozoline) is first administered to vessels surrounding the target site to minimize leakage of the priming or secondary agents.

A priming agent of proscillaridin at a concentration of 0.0001-10 mM in a volume of 0.05-2 cc is then administered at a nerve proximal site to prime the neurons by inhibiting the transport of potassium and sodium across the nerve cell membrane and subsequently inducing an intracellular calcium flux.

Approximately 0.1-20 minutes later, a secondary agent of domoic acid at a concentration of 0.00005-0.005 mM in a volume of 0.05-2 cc is then administered at a nerve proximal site to induce neuronal excitotoxicity.

Proscillaridin binds to a site on the extracellular aspect of the α-subunit of the Na+/K+ ATPase pump in the membranes of heart cells (myocytes) and decreases its function. This causes an increase in the level of sodium ions in the myocytes, which leads to a rise in the level of intracellular calcium ions. This occurs because of a sodium/calcium exchanger on the plasma membrane, which depends on a constant inward sodium gradient to pump out calcium. Proscillaridin decreases sodium concentration gradient and the subsequent calcium outflow, thus raising the calcium concentration in myocardiocytes and pacemaker cells.

Increased intracellular calcium lengthens Phase 4 and Phase 0 of the cardiac action potential, which leads to a decrease in heart rate. Increased amounts of Ca2+ also leads to increased storage of calcium in the sarcoplasmic reticulum, causing a corresponding increase in the release of calcium during each action potential. This leads to increased contractility, the force of contraction, of the heart.

There is also evidence that proscillaridin increases vagal activity, thereby decreasing heart rate by slowing depolarization of pacemaker cells in the AV node. This negative chronotropic effect would therefore be synergistic with the direct effect on cardiac pacemaker cells. Proscillaridin and other bufadienolides are not used widely in the United States, but are used in Europe to treatment of various arrhythmias.

Domoic acid can bioaccumulate in marine organisms such as shellfish, anchovies, and sardines that feed on the phytoplankton known to produce this toxin. DA can accumulate in high concentrations in the tissues of these plankton feeders when the toxic phytoplankton itself is high in concentration in the surrounding waters. In mammals, including humans, domoic acid acts as a neurotoxin, causing short-term memory loss, brain damage and, in severe cases, death. DA-producing algal blooms are associated with the phenomenon of amnesic shellfish poisoning (ASP).

In marine mammals, domoic acid typically causes seizures and tremors. In the brain, domoic acid especially damages the hippocampus and amygdaloid nucleus. It damages the neurons by activating AMPA and kainate receptors, causing an influx of calcium. Although calcium flowing into cells is a normal event, the uncontrolled increase of calcium causes the cell to degenerate. Because the hippocampus may be severely damaged, short-term memory loss occurs.

EXAMPLE 3

A vasoconstrictor (antidiuretic hormone (ADH or vasopressin) or tetrahydrozoline) is first administered to vessels surrounding the target site to minimize leakage of the priming or secondary agents.

A priming agent of N-Methyl-D-aspartic acid (NMDA) at a concentration of 0.01-300 mM in a volume of 0.05-2 cc is then administered at a nerve proximal site to prime the neurons by inducing excitatory intracellular signaling.

Approximately 0.1-20 minutes later, a secondary agent of digoxin at a concentration of 0.0001-10 mM in a volume of 0.05-2 cc is then administered at a nerve proximal site to inhibit the transport of potassium and sodium across the nerve cell membrane and subsequently induce high levels of intracellular calcium to mediate pro-apoptotic signaling and neuronal toxicity.

N-Methyl-D-aspartic acid (NMDA) is an amino acid derivative, which acts as a specific agonist at the NMDA receptor mimicking the action of glutamate, the neurotransmitter, which normally acts at that receptor. Unlike glutamate, NMDA only binds to and regulates the NMDA receptor and has no effect on other glutamate receptors (such as those for AMPA and kainate). NMDA receptors are particularly important when they become overactive during withdrawal from alcohol as this causes symptoms such as agitation and, sometimes, epileptiform seizures.

NMDA is a water-soluble synthetic substance that is not normally found in biological tissue. NMDA is an excitotoxin; this trait has applications in behavioral neuroscience research. The body of work utilizing this technique falls under the term "lesion studies." Researchers apply NMDA to specific regions of an (animal) subject's brain or spinal cord and subsequently test for the behavior of interest, such as operant behavior. If the behavior is compromised, it suggests the destroyed tissue was part of a brain region that made an important contribution to the normal expression of that behavior. However, in lower quantities NMDA is not neurotoxic. Therefore the action of glutamate specifically through NMDA receptors can be investigated by injecting small quantities of NMDA into a certain region in the brain: for example, injection of NMDA in a brainstem region induces involuntary locomotion in cats and rats.

EXAMPLE 4

A vasoconstrictor (antidiuretic hormone (ADH or vasopressin) or tetrahydrozoline) is first administered to vessels surrounding the target site to minimize leakage of the priming or secondary agents.

A priming agent of verapamil at a concentration of 0.1-600 mM in a volume of 0.05-2 cc is then administered at a nerve proximal site to interrupt potassium and sodium transport across the nerve cell membrane and prime the neurons by blocking calcium channels and inducing an intracellular signaling.

Approximately 0.1-20 minutes later, a secondary agent of carbamazepine at a concentration of 10-500 mM or lithium at a concentration of 0.5-400 mM in a volume of 0.05-2 cc is then administered at a nerve proximal site to interrupt potassium and sodium transport across the nerve cell membrane and induce neuronal toxicity.

Verapamil (brand names: Isoptin, Verelan, Verelan PM, Calan, Bosoptin, Covera-HS) is an L-type calcium channel blocker of the phenylalkylamine class. It has been used in the treatment of hypertension, angina pectoris, cardiac arrhythmia, and most recently, cluster headaches. It is also an effective preventive medication for migraine. Verapamil has also been used as a vasodilator during cryopreservation of blood vessels. It is a class 4 anti-arrhythmic, more effective than digoxin in controlling ventricular rate. Verapamil's mechanism in all cases is to block voltage-dependent calcium channels.

In cardiac pharmacology, calcium channel blockers are considered class IV anti-arrhythmic agents. Since calcium channels are especially concentrated in the sinoatrial and atrio-ventricular nodes, these agents can be used to decrease impulse conduction through the AV node, thus protecting the ventricles from atrial tachy arrhythmias.

Calcium channels are also present in the smooth muscle that lines blood vessels. By relaxing the tone of this smooth muscle, calcium-channel blockers dilate the blood vessels. This has led to their use in treating hypertension and angina pectoris. The pain of angina is caused by a deficit in oxygen supply to the heart. Calcium channel blockers like verapamil will dilate blood vessels, which increases the supply of blood and oxygen to the heart. This controls chest pain, but only when used regularly. It does not stop chest pain once it starts. A more powerful vasodilator such as nitroglycerin may be needed to control pain once it starts. Verapamil is also used intra-arterially to treat cerebral vasospasm and cluster headaches.

Carbamazepine exhibits autoinduction: it induces the expression of the hepatic microsomal enzyme system CYP3A4, which metabolizes carbamazepine itself. Upon initiation of carbamazepine therapy, concentrations are predictable and follow their respective baseline clearance/half-life values that have been established for the specific patient. However, after enough carbamazepine has been presented to the liver tissue, the CYP3A4 activity increases, speeding up drug clearance and shortening the half-life. Auto-induction will continue with subsequent increases in dose but will usually reach a plateau within 5-7 days of a maintenance dose. Increases in dose at a rate of 200 mg every 1-2 weeks may be required to achieve a stable seizure threshold. Stable carbamazepine concentrations occur usually within 2-3 weeks after initiation of therapy. The mechanism of action of carbamazepine and its derivatives is relatively well understood. Voltage-gated sodium channels are the molecular pores that allow brain cells (neurons) to generate action potentials, the electrical events that allow neurons to communicate over long distances. After the sodium channels open to start the action potential, they inactivate, essentially closing the channel. Carbamazepine stabilizes the inactivated state of sodium channels, meaning that fewer of these channels are available to subsequently open, making brain cells less excitable (less likely to fire). Carbamazepine has also been shown to potentiate GABA receptors made up of alpha1, beta2, gamma2 subunits.

Lithium salts such as lithium carbonate (Li2CO3), lithium citrate, and lithium orotate are mood stabilizers. They are used in the treatment of bipolar disorder since, unlike most other mood altering drugs, they counteract both depression and mania (though more effective for the latter). Lithium continues to be the gold standard for the treatment of bipolar disorder. It is also helpful for related diagnoses, such as schizoaffective disorder and cyclic major depression. In addition to watching out for the well-known complications of lithium treatment—hypothyroidism and decreased renal function—health care providers should be aware of hyperparathyroidism. Lithium can also be used to augment antidepressants. Because of lithium's nephrogenic diabetes insipidus effects, it can be used to help treat the syndrome of inappropriate antidiuretic hormone hypersecretion (SIADH). It was also sometimes prescribed as a preventive treatment for migraine disease and cluster headaches.

The active principle in these salts is the lithium ion Li+. Although this ion has a smaller diameter than either Na+ or K+, in a watery environment like the cytoplasmic fluid, Li+ binds to the oxygen atoms of water, making it effectively larger than either Na+ or K+ ions. How Li+ works in the central nervous system is still a matter of debate. Li+ elevates brain levels of tryptophan, 5-HT (serotonin), and 5-HIAA (a serotonin metabolite). Serotonin is related to mood stability. Li+ also reduces catecholamine activity in the brain (associated with brain activation and mania), by enhancing reuptake and reducing release. Therapeutically useful amounts of lithium (1.0 to 1.2 mmol/L) are only slightly lower than toxic amounts (>1.5 mmol/L), so the blood levels of lithium must be carefully monitored during treatment to avoid toxicity.

EXAMPLE 5

A vasoconstrictor (antidiuretic hormone (ADH or vasopressin) or tetrahydrozoline) is first administered to vessels surrounding the target site to minimize leakage of the priming or secondary agents.

A priming agent of digoxin at a concentration of 0.0001-10 mM in a volume of 0.05-2 cc is then administered at a nerve proximal site to prime the neurons by inducing an intracellular calcium flux.

Approximately 0.1-20 minutes later, a secondary agent of tetrodotoxin, hoiamide, or ω-conotoxin, each at a concentration of 0.00005-0.001 mM, in a volume of 0.05-0.5 cc is then administered at a nerve proximal site to block ion channels and induce neuronal toxicity.

Tetrodotoxin has been isolated from widely differing animal species, including western newts of the genus *Taricha* (where it was termed "tarichatoxin"), pufferfish, toads of the genus *Atelopus*, several species of blue-ringed octopodes of the genus *Hapalochlaena* (where it was called "maculotoxin"), several sea stars, certain angelfish, a polyclad flatworm, several species of *Chaetognatha* (arrow worms), several nemerteans (ribbonworms) and several species of xanthid crabs. The toxin is variously used as a defensive biotoxin to ward off predation, or as both a defensive and predatory venom (the octopodes, chaetognaths and ribbonworms). Tarichatoxin and maculotoxin were shown to be identical to tetrodotoxin in 1964 and 1978, respectively. Recent evidence has shown the toxin to be produced by bacteria within blue-ringed octopuses. The most common source of bacteria associated with TTX production is *Vibrio* bacteria, with *Vibrio alginolyticus* being the most common species. Pufferfish, chaetognaths, and nemerteans have been shown to contain *Vibrio alginolyticus* and TTX.

Tetrodotoxin binds to what is known as site 1 of the fast voltage-gated sodium channel. Site 1 is located at the extracellular pore opening of the ion channel. The binding of any molecules to this site will temporarily disable the function of the ion channel. Saxitoxin and several of the conotoxins also bind the same site. The use of this toxin as a biochemical probe has elucidated two distinct types of voltage-gated sodium channels present in humans: the tetrodotoxin-sensitive voltage-gated sodium channel (TTX-s Na+ channel) and the tetrodotoxin-resistant voltage-gated sodium channel (TTX-r Na+ channel). Tetrodotoxin binds to TTX-s Na+ channels with a binding affinity of 5-15 nanomolar, while the TTX-r Na+ channels bind TTX with low micromolar affinity. Nerve cells containing TTX-r Na+ channels are located primarily in cardiac tissue, while nerve cells containing TTX-s Na+ channels dominate the rest of the body. The prevalence of TTX-s Na+ channels in the central nervous system makes tetrodotoxin a valuable agent for the silencing of neural activity within a cell culture.

The toxin blocks the fast Na+ current in human myocytes (the contractile cells of the muscles), thereby inhibiting their contraction. By contrast, the sodium channels in pacemaker cells of the heart are of the slow variety, so action potentials in the cardiac nodes are not inhibited by the compound. The myocytes in the atrium, which surround the main cardiac pacemaker, do express this fast Na+ current and therefore the electrical activity is blocked and the heart fails to beat.

A conotoxin is one of a group of neurotoxic peptides isolated from the venom of the marine cone snail, genus *Conus*. Conotoxins, which are peptides consisting of 10 to 30 amino acid residues, typically have one or more disulfide bonds. Conotoxins have a variety of mechanisms of actions, most of which have not been determined. Many of these peptides modulate the activity of ion channels.

ω-conotoxins have a knotting or inhibitor cysteine knot scaffold. The knotting scaffold is a very special disulfide-through-disulfide knot, in which the III-VI disulfide bond crosses the macrocycle formed by two other disulfide bonds (I-IV and II-V) and the interconnecting backbone segments, where I-VI indicates the six-cysteine residues starting from the N-terminus. The cysteine arrangements are the same for omega, delta and kappa families, even though omega conotoxins are calcium channel blockers, whereas delta conotoxins delay the inactivation of sodium channels, and kappa conotoxins are potassium channel blockers. Ziconotide is derived from the toxin of the cone snail species *Conus magus*.

The following table lists agents and examples of concentrations for which they may be used for denervation at a volume of approximately 2 cc.

| AGENT | CAS NUMBER | MW | CONCENTRATION RANGE |
|---|---|---|---|
| Digoxin | 20830-75-5 | 780.94 g/mol | 0.01-10 microM |
| Staurosporine | 62996-74-1 | 466.54 g/mol | 0.1-100 microM |
| Amlodipine | 88150-42-9 | 408.88 g/mol | 0.25-250 microM |
| Verapamil | 52-53-9 | 454.60 g/mol | 0.1-500 microM |
| Cymarin | 508-77-0 | 548.66 g/mol | 0.1-10 microM |
| Digitoxin | 71-63-6 | 764.94 g/mol | 0.1-10 microM |
| Proscillaridin | 466-06-8 | 530.65 g/mol | 0.1-10 microM |
| Ouabain | 630-60-4 | 584.65 g/mol | 0.01-10 microM |
| Veratridine | 71-62-5 | 673.79 g/mol | 10-100 microM |
| Glutamate | 617-65-2 | 147.13 g/mol | 0.1-800 microM |
| Domoic acid | 14277-97-5 | 311.33 g/mol | 0.01-100 microM |
| Oleandrin | 465-16-7 | 576.72 g/mol | 0.01-10 microM |
| Carbamazepine | 298-46-4 | 236.27 g/mol | 1-900 microM |

FIG. 10A shows the amount of cell death caused by several of agents for a fixed amount of time. Primary nerve cell death was measured using percent trypan blue positive. Primary nerve cells were incubated in the presence of the agents for 15 minutes, washed with fresh media, and incubated for 30 minutes at 37° C. prior to trypan blue scoring. Cell death was assessed by the percentage of cells in the field that were trypan blue positive. Three hundred cells per condition (100 cells per well, 3 wells per condition) were counted using a light microscope.

FIG. 10B shows the amount of cell death caused by several agents versus time. Primary nerve cells were incubated at 37° C. in the presence of the agents for 5, 10, 30, and 60 minutes, washed with fresh media, and evaluated by trypan blue scoring. Cell death was assessed by the percent of cells in the field that were trypan blue positive. Three hundred cells per condition (100 cells per well, 3 wells per condition) were counted using a light microscope.

The description and examples given above describe the denervation of renal nerves surrounding the renal arteries to control hypertension. However, the described devices, methods, agents and delivery methods may be used to treat other diseases. These include and are not limited to diabetes (insulin production levels), fibromyalgia, pain management, and obesity.

While the foregoing has been with reference to particular embodiments of the invention, it will be appreciated by those skilled in the art that changes in these embodiments may be made without departing from the principles and spirit of the invention.

What is claimed is:

1. A method for killing targeted renal nerve cells in a mammal, the method comprising:
    delivering a cardiac glycoside locally to the renal nerve cells in an amount sufficient to potentiate the toxicity effects of an excitatory signal induced by glutamate;
    delivering glutamate locally to the renal nerve cells in an amount sufficient to overstimulate the renal nerve cells to promote apoptosis of the renal nerve cells and treat hypertension in the mammal.

2. The method of claim 1, wherein the cardiac glycoside is digoxin, proscillaridin, or ouabin.

3. The method of claim 1, further comprising:
    delivering digoxin immune Fab to tissue surrounding the renal nerve cells, the digoxin immune Fab being capable of neutralizing any excess cardiac glycoside.

4. The method of claim 1, further comprising:
    delivering an anesthetic to tissue surrounding the renal nerve cells before delivering the cardiac glycoside.

5. The method of claim 1, further comprising:
    delivering saline to tissue surrounding the renal nerve cells to flush any excess cardiac glycoside or glutamate.

6. A method for killing targeted renal nerve cells in a mammal, the method comprising:
    delivering a cardiac glycoside locally to the renal nerve cells in an amount sufficient to potentiate the toxicity effects of carbamazepine; and
    delivering carbamazepine locally to the renal nerve cells in an amount sufficient to block an action potential and repolarization of the renal nerve cells to kill the renal nerve cells and treat hypertension in the mammal.

7. The method of claim 6, wherein the cardiac glycoside is digoxin, proscillaridin, or ouabin.

8. The method of claim 6, further comprising:
    delivering digoxin immune Fab to tissue surrounding the renal nerve cells, the digoxin immune Fab being capable of neutralizing any excess cardiac glycoside.

9. The method of claim 6, further comprising:
    delivering an anesthetic to tissue surrounding the renal nerve cells before delivering the cardiac glycoside.

10. The method of claim 6, further comprising:
    delivering saline to tissue surrounding the renal nerve cells to flush any excess cardiac glycoside.

* * * * *